(12) United States Patent
Okuno et al.

(10) Patent No.: US 10,219,813 B2
(45) Date of Patent: Mar. 5, 2019

(54) JIG FOR GUIDE PIN PIERCING

(71) Applicants: TEIJIN MEDICAL TECHNOLOGIES CO., LTD, Osaka (JP); NATIONAL UNIVERSITY CORPORATION KOBE UNIVERSITY, Hyogo (JP)

(72) Inventors: Masaki Okuno, Osaka (JP); Hiroshi Morii, Osaka (JP); Katsuya Nada, Osaka (JP); Ryo Kashiwadani, Osaka (JP); Ryosuke Kuroda, Hyogo (JP)

(73) Assignees: TEIJIN MEDICAL TECHNOLOGIES CO., LTD., Osaka (JP); NATIONAL UNIVERSITY CORPORATION KOBE UNIVERSITY, Hyogo (JP)

( * ) Notice: Subject to any disclaimer, the term of this patent is extended or adjusted under 35 U.S.C. 154(b) by 644 days.

(21) Appl. No.: 14/548,390

(22) Filed: Nov. 20, 2014

(65) Prior Publication Data
US 2015/0150570 A1  Jun. 4, 2015

(30) Foreign Application Priority Data

Nov. 22, 2013 (JP) .................................. 2013-241760

(51) Int. Cl.
*A61B 17/17* (2006.01)
(52) U.S. Cl.
CPC ...... *A61B 17/1764* (2013.01); *A61B 17/1714* (2013.01)
(58) Field of Classification Search
CPC .......................... A61B 17/1721; A61B 17/1725
See application file for complete search history.

(56) References Cited

U.S. PATENT DOCUMENTS

| 6,120,511 A | 9/2000 | Chan |
| 2003/0216742 A1 | 11/2003 | Wetzler et al. |

(Continued)

FOREIGN PATENT DOCUMENTS

| JP | 5-95507 | 12/1993 |
| JP | 2001-525210 | 12/2001 |

(Continued)

OTHER PUBLICATIONS

Japanese Notification of Reasons for Refusal, dated May 25, 2015, in corresponding Japanese Appln. No. 2013-241760, and English translation thereof.

*Primary Examiner* — David W Bates
(74) *Attorney, Agent, or Firm* — Wenderoth, Lind & Ponack, L.L.P.

(57) ABSTRACT

A guide pin piercing jig includes a curved frame, a front cylinder unit provided at a front end of the frame, and a rear cylinder unit provided at a rear end of the frame, in which the front cylinder unit has a positioning projection and a boring aiming portion at a tip thereof, the rear cylinder unit has a plurality of parallel guide pin insertion cylinders into which to insert the guide pins and a tentative fixing unit provided at a tip of the rear cylinder unit, and the rear cylinder unit is provided at a rear end of the frame slidably so as be directed to a tip of the front cylinder unit. It becomes possible to aim at a proper portion of a living body bone through which to bore a bone tunnel and to pierce the living body bone with guide pins for hollow drills from behind the living body bone to the proper aiming portion in a proper direction.

13 Claims, 23 Drawing Sheets

(56) References Cited

U.S. PATENT DOCUMENTS

| | | |
|---|---|---|
| 2009/0216236 A1 | 8/2009 | Re |
| 2012/0109136 A1* | 5/2012 | Bourque ............ A61B 17/1714 606/87 |
| 2013/0023891 A1 | 1/2013 | Berberich et al. |
| 2013/0030442 A1 | 1/2013 | Pilgeram et al. |
| 2013/0053959 A1* | 2/2013 | Lizardi .............. A61B 17/1714 623/13.14 |

FOREIGN PATENT DOCUMENTS

| | | |
|---|---|---|
| JP | 2009-195701 | 9/2009 |
| JP | 2011-509749 | 3/2011 |
| JP | 2013-043093 | 3/2013 |
| WO | 99/29237 | 6/1999 |
| WO | 2009/094239 | 7/2009 |
| WO | 2012/122497 | 9/2012 |

* cited by examiner

JIG FOR GUIDE PIN PIERCING

BACKGROUND OF THE INVENTION

1. Technical field

The present invention relates to a jig to be used for piercing a living body bone with a guide pin for a boring hollow drill. More specifically, the present invention relates to a guide pin piercing jig which is used for piercing a joint bone with a guide pin for a hollow drill in such a manner that, for example, in reconstruction of a torn anterior curuciate ligament, the position and direction of the guide pin are determined correctly according to the intension of a doctor in boring, through the joint bone, by the hollow drill, a bone tunnel that is necessary to transplant a tendon acquired from another part in the knee joint or the like 2. Description of the Related Art As is well known, in reconstruction of a torn anterior cruciate ligament (ACL), it is necessary to bore, through a bone of the knee joint at a proper location, a bone tunnel that is necessary to transplant a tendon acquired from another part in the knee joint.

As a device used for such ACL reconstruction, proposed is a device for determining a position of a second bone tunnel to be bored through a shinbone top portion of the knee joint on the basis of a first bone tunnel that has been bored through a thighbone bottom portion of the knee joint (JP-A-2009-195701).

This device includes: a long and narrow main body having a near end and a far end; an arm which extends from the far end of the main body at a certain angle; a spherical tip portion formed at a far end of the arm; and an outrigger provided at the near end of the main body, and the device is configured to permit the following operation. When the spherical tip portion of the device is inserted into a first bone tunnel that has been bored through a thighbone bottom portion of the knee joint and serves as a reference, the arm indicates a proper position and angle of a second bone tunnel to be bored through a shinbone top portion. A second bone tunnel can be formed at a proper angle at a proper position of the shinbone top portion by boring it by a hollow drill along a guide wire that is stuck into the shinbone top portion from a wire insertion cylinder of the outrigger.

SUMMARY OF THE INVENTION

In the device of JP-A-2009-195701, as described above, when a reference first bone tunnel is bored through a thighbone bottom portion of the knee joint, a proper position and angle of a second bone tunnel to be bored through a shinbone top portion of the knee joint can be determined by inserting the spherical tip portion into the first bone tunnel. However, this device has a problem that a proper position and angle of a second bone tunnel to be bored through a shinbone top portion cannot be determined in the case where no first bone tunnel is bored through a thighbone bottom portion of the knee joint.

The device of Patent document 1 has another problem that a position and an angle of a first bone tunnel to be bored through a thighbone bottom portion of the knee joint cannot be determined properly irrespective of whether a second bone tunnel is formed through a shinbone top portion of the knee joint.

Incidentally, in existing ACL reconstruction techniques, it is a common procedure to bore a bone tunnel through a shinbone top portion of the knee joint obliquely upward by a hollow drill from its front surface side and to insert a hollow drill into the knee joint and bore a bone tunnel through a thighbone bottom portion obliquely upward from its bottom surface side. However, where a bone tunnel is bored from the bottom surface side of a thighbone bottom portion, since the bottom surface of the thighbone bottom portion is curved and a portion suitable for boring of a bone tunnel has a curved slant surface, it is not easy to stick the guide wire (guide pin) for the hollow drill into the proper portion in a proper direction. This raises a problem that it is difficult to bore a bone tunnel through the proper portion in a proper direction from the bottom surface side of the thighbone bottom portion by the hollow drill being guided by the guide wire.

Furthermore, the position of a bone tunnel that has been bored by the above method of boring it obliquely upward from the bottom surface side of the thighbone bottom portion by inserting the hollow drill into the knee joint is much deviated from the position of the anterior cruciate ligament of the living body. It is therefore desired to fix a replacement ligament (transplantation tendon) at the natural living body ligament position.

The present invention has been made in the above circumstances, and an object of the present invention is therefore to provide a guide pin piercing jig which make it possible to aim at a proper portion of a living body bone through which to bore a bone tunnel even if no reference bone tunnel is bored and to pierce the living body bone with a guide pin for a hollow drill from behind the living body bone to the proper aiming portion in a proper direction, to thereby make it possible to bore a bone tunnel through the living body bone by the hollow drill that is guided by the guide pin inserted therein, from behind the living body bone to a proper portion of the living body bone in a proper direction.

To attain the above object, a guide pin piercing jig according to the present invention is a guide pin piercing jig for piercing a living body bone with guide pins for boring hollow drills in such a manner as to determine positions and a direction of the guide pins, which includes: a curved frame; a front cylinder unit provided at a front end of the frame; and a rear cylinder unit provided at a rear end of the frame. The front cylinder unit has a positioning projection and a boring aiming portion at a tip thereof, the rear cylinder unit has a plurality of parallel guide pin insertion cylinders into which to insert the guide pins and a tentative fixing unit provided at a tip of the rear cylinder unit, and the rear cylinder unit is provided at a rear end of the frame slidably so as be directed to a tip of the front cylinder unit.

In a guide pin piercing jig according to the present invention, it is desirable that the respective center axes of the plurality of parallel guide pin insertion cylinders of the rear cylinder unit pass through the boring aiming portion provided at the tip of the front cylinder unit. It is also desirable that the boring aiming portion has an opening. It is also desirable that a tip surface of the boring aiming portion is inclined from a center axis of the front cylinder unit.

In a guide pin piercing jig according to the present invention, it is desirable that the front cylinder unit is attached to the front end of the frame in a detachable manner, or that the rear cylinder unit is attached to the rear end of the frame in a detachable manner. It is also desirable that each of the front cylinder unit and the plurality of guide pin insertion cylinders of the rear cylinder unit has a straight cylinder hole. It is also desirable that a center axis of the front cylinder unit and each of center axes of the plurality of guide pin insertion cylinders of the rear cylinder unit cross each other at an angle of larger than 90° and smaller than 180°.

A guide pin piercing jig according to the present invention makes it possible to pierce a living body bone with plural guide pins in a proper direction from behind to a proper portion of the living body bone through which to bore a bone tunnel, by: applying the boring aiming portion at the tip of the front cylinder unit to a proper portion of the living bone through which to bore a bone tunnel so as to position the front cylinder unit with the positioning projection; tentatively fixing tips of the plural parallel guide pin insertion cylinders of the rear cylinder unit to the back surface of the living body bone by sliding the guide pin insertion cylinders from behind the living body bone; and, in this state, piercing the living body bone with guide pins for hollow drills by inserting them into guide pin insertion cylinders from their rear ends until they reach the boring aiming portion of the front cylinder unit. Therefore, by boring the living boy bone from behind by the hollow drills being guided by the respective guide pins, plural bone tunnels (through-holes) can be formed in the proper portion and in the proper direction.

As described later, the reason why plural bone tunnels are bored through a living body bone by piercing it with plural guide pins as with a guide pin piercing jig according to the present invention is to form, in a later step, a rectangular or elliptical bone tunnel that is different from an existing circular bone tunnel and suitable for tendon transplantation, by inserting a center drill guide into the bone tunnels, and by boring another tunnel between the two bone tunnels with a center drill inserted into the center drill guide to connect the two bone tunnels, and expanding the connected bone tunnel into a rectangular or elliptical shape with a dilator or subjecting it to chiseling.

As described above, a guide pin piercing jig according to the present invention makes it possible to apply the boring aiming portion of the front cylinder unit to a proper portion of a living body bone through which to bore a bone tunnel and to pierce the living body bone with guide pins for hollow drills from behind to a proper portion of the living body bone in a proper direction. For example, in a case of boring bone tunnels for tendon transplantation through a thighbone bottom portion of the knee joint in ACL reconstruction, plural guide pins can pierce the thighbone bottom portion through which to bore a bone tunnel from obliquely behind to a proper portion in a proper direction by inserting the front cylinder unit of the jig into the knee joint from the front side, positioning the tip boring aiming portion of the front cylinder unit by applying it to a proper portion (i.e., a portion, having a curved slant surface, of a thighbone bottom surface), through which to bore a bone tunnel, of the thighbone bottom portion, and piercing the thighbone bottom portion with guide pins from the plural guide pin insertion cylinders of the rear cylinder unit until they reach the boring aiming portion of the front cylinder unit in the same manner as described above. Therefore, by boring the thighbone bottom portion by hollow drills from obliquely behind along the respective guide pins, plural bone tunnels can be formed in a proper direction so as to reach a proper portion (i.e., a portion, having a curved slant surface) of the thighbone bottom surface) of the thighbone bottom portion. In subsequently steps, the plural bone tunnels are connected to each other by boring a tunnel between them and a connected bone tunnel is subjected to cutting into a rectangular or elliptical shape. As a result, a rectangular or elliptical bone tunnel that is suitable for tendon transplantation can be formed.

In a guide pin piercing jig according to the present invention in which the respective center axes of the plural parallel guide pin insertion cylinders of the rear cylinder unit pass through the boring aiming portion provided at the tip of the front cylinder unit, guide pins that are inserted into the respective guide pin insertion cylinders reach the boring aiming portion of the front cylinder unit reliably and pierce a living body bone in a proper direction from obliquely behind to a proper portion to which the boring aiming portion is applied and to which to bore a bone tunnel. Therefore, bone tunnels can be bored reliably through the living body bone from obliquely behind to its proper portion in a proper direction by hollow drills along the guide pins, respectively.

Where the boring aiming portion has an opening, reaching of the tips of guide pins to the boring aiming portion can be confirmed by observing entrance into the opening of the tips of the guide pins that have been pierced through a living body bone from behind with a fiber scope or the like.

Where a tip surface of the boring aiming portion is inclined from the center axis of the front cylinder unit, the inclined tip surface of the boring aiming portion can be applied stably to (so as to conform to) a curved slant surface of a portion of a thighbone bottom portion to which bone tunnels are to be bored when, for example, the front cylinder unit is inserted into the knee joint from the front side.

Where the front cylinder unit is attached to the front end of the frame in a detachable manner or the rear cylinder unit is attached to the rear end of the frame in a detachable manner, the guide pin piercing jig can be carried easily in a state that the frame is separated from the front cylinder unit or the rear cylinder unit and can be assembled easily and used at a medical treatment site. Where each of the front cylinder unit and the plural guide pin insertion cylinders of the rear cylinder unit has a straight cylinder hole, guide pin piercing work is facilitated.

Where the center axis of the front cylinder unit and each of center axes of the plural guide pin insertion cylinders of the rear cylinder unit cross each other at an angle of larger than 90° and smaller than 180°, guide pins can be pierced properly through, in particular, a thighbone bottom portion of the knee joint.

BRIEF DESCRIPTION OF THE DRAWINGS

FIG. 10A shows a state before insertion of the guide pin insertion cylinder into the insertion hole, FIG. 10B shows a state that a tip portion of the guide pin insertion cylinder is inserted in the insertion hole, and FIG. 10C shows a state that the guide pin insertion cylinder is inserted halfway in the insertion hole.

FIG. 11A shows a state that guide pin insertion cylinder is rotated by 180° and FIG. 11B shows a state that the guide pin insertion cylinder is pulled out halfway.

FIG. 25A shows a state that the guide pin insertion cylinders are locked so as not to be slidable rearward and FIG. 25B shows a state the guide pin insertion cylinders are unlocked so as to be slidable rearward.

DETAILED DESCRIPTION OF THE INVENTION

Guide pin piercing jigs according to embodiments of the present invention will be hereinafter described in detail with reference to the drawings.

Figure 1:
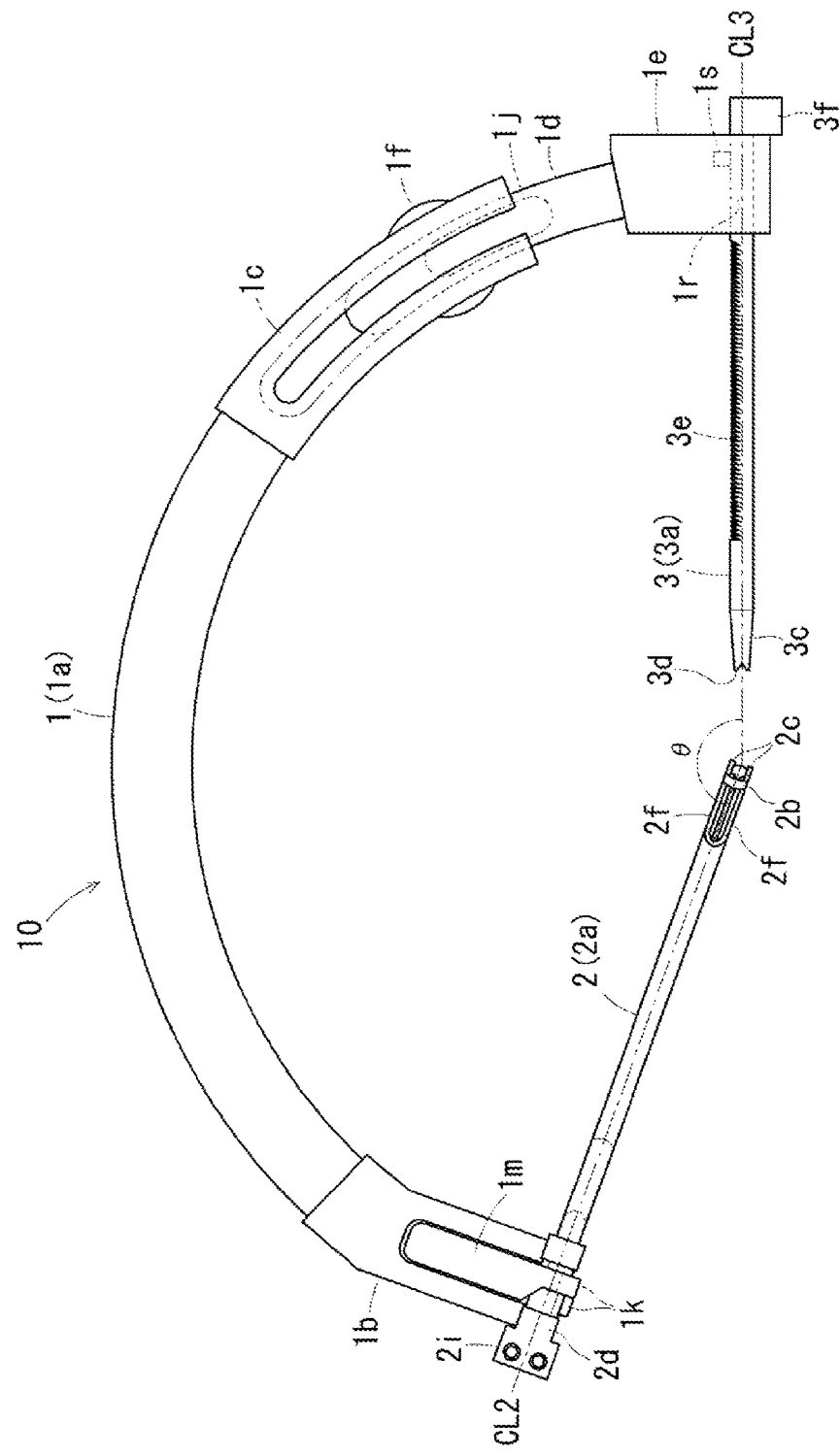
FIG. 1 is a side view of a guide pin piercing jig according to an embodiment of the present invention.
Figure 2:
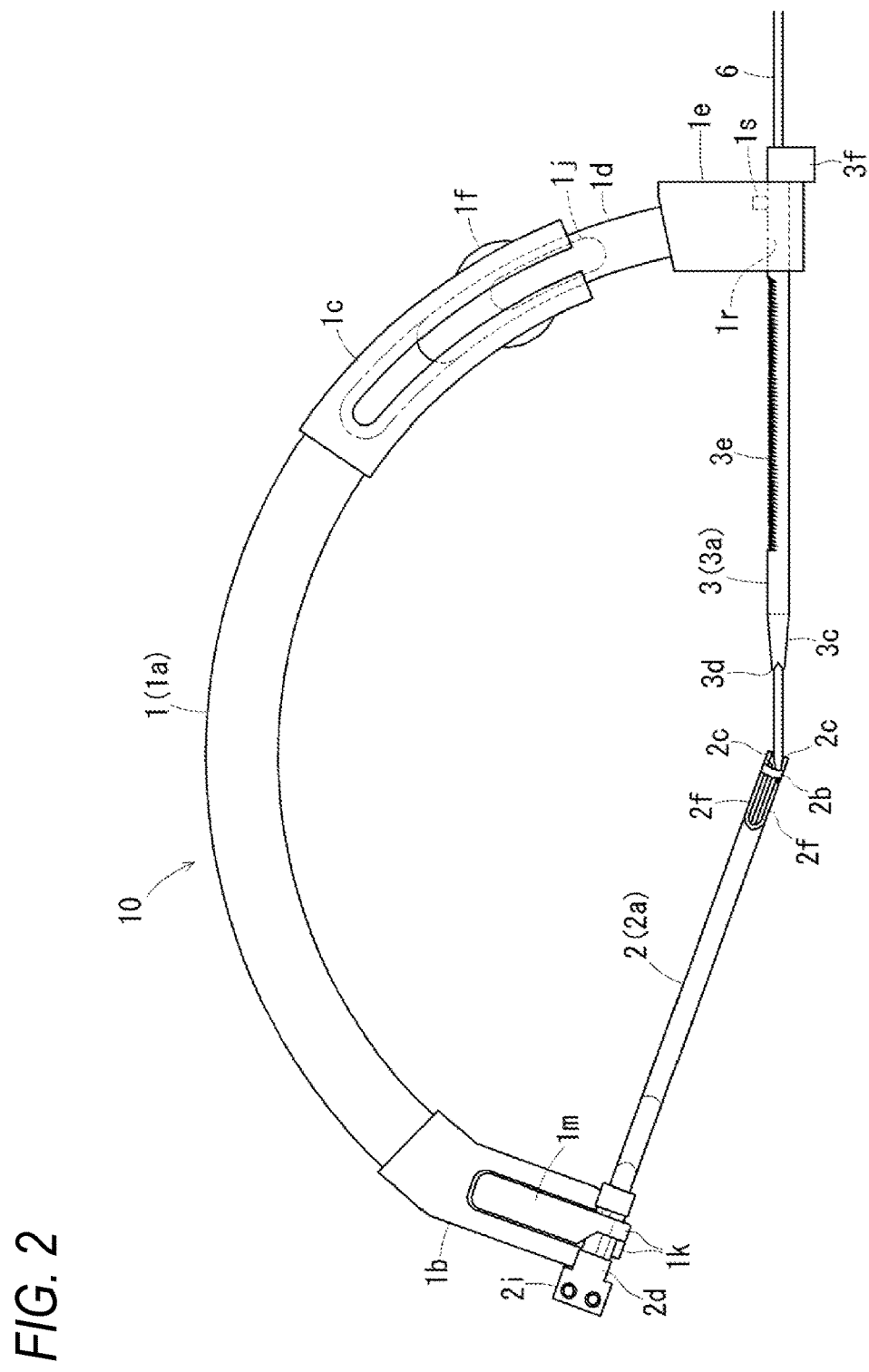
FIG. 2 is a side view showing a state that guide pins for hollow drills are inserted in guide pin insertion cylinders of a rear cylinder unit of the guide pin piercing jig.
Figure 3:
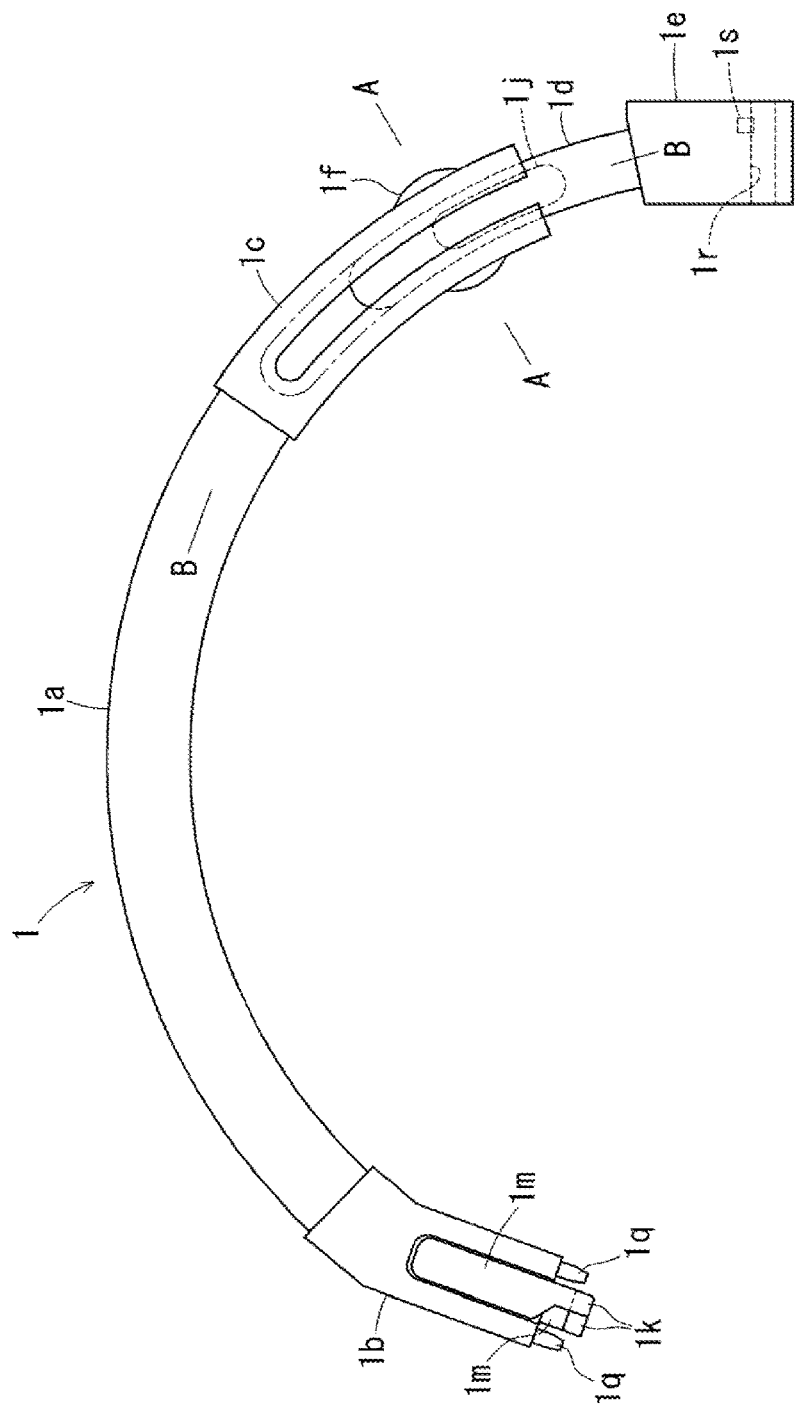
FIG. 3 is a side view of a frame of the guide pin piercing jig.
Figure 4:
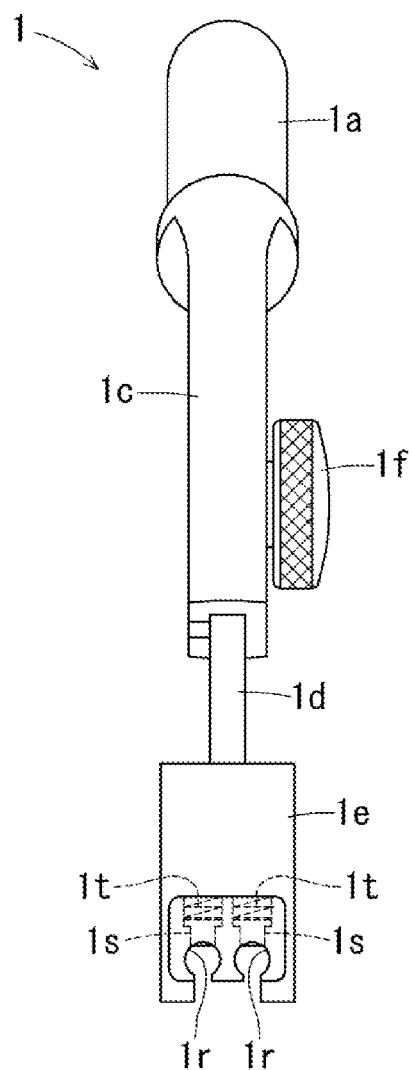
FIG. 4 is a rear view of the frame.
Figure 5:
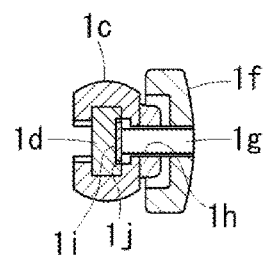
FIG. 5 shows an end view of cutting FIG. 3 along the A-A.
Figure 6:
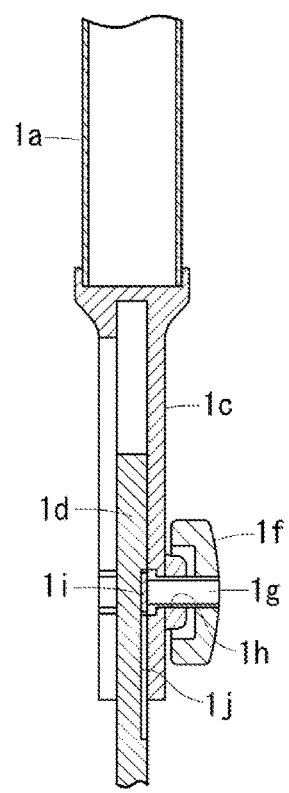
FIG. 6 shows an end view of cutting FIG. 3 along the line B-B.
Figure 7:
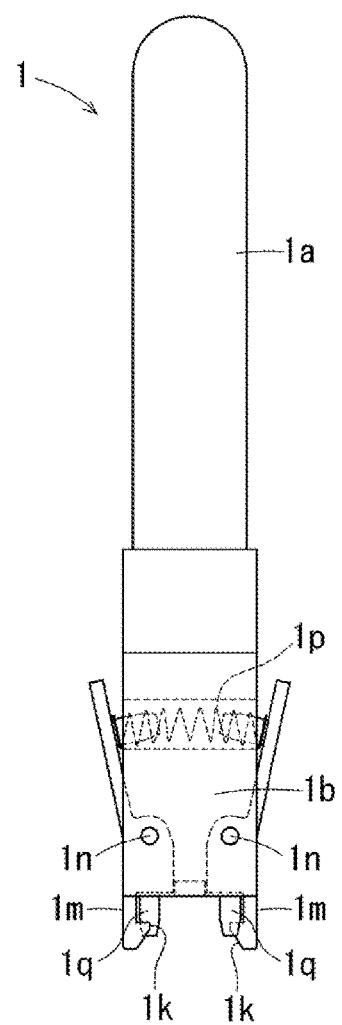
FIG. 7 shows the frame as viewed from above and the front side.
Figure 8A:
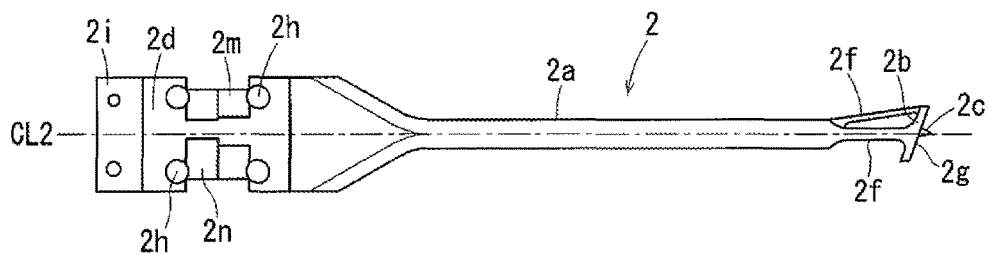
FIG. 8A is a plan view of a front cylinder unit.
Figure 8B:
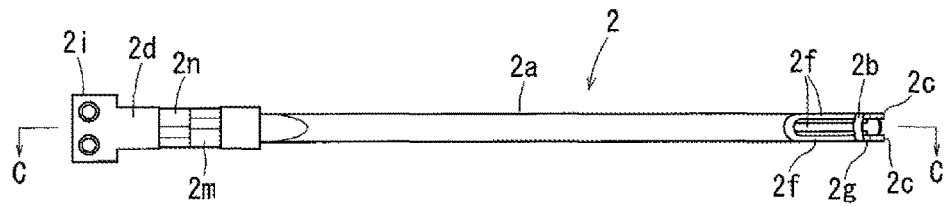
FIG. 8B is a side view of the front cylinder unit.
Figure 8C:
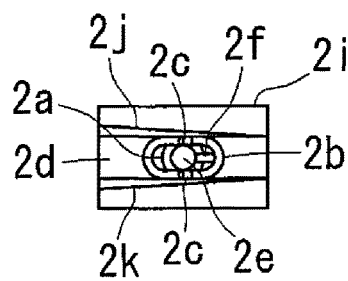
FIG. 8C is a front view of the front cylinder unit.
Figure 8D:
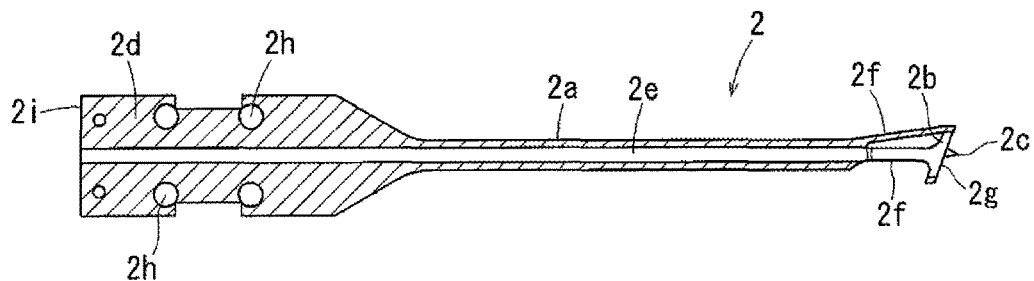
FIG. 8D is a sectional view taken along the line C-C in FIG. 8B
Figure 9A:
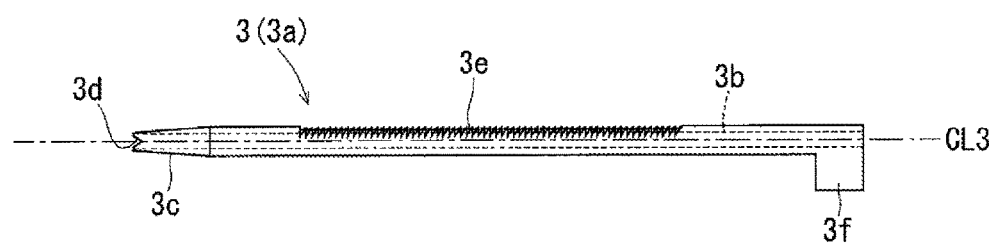
FIG. 9A is a side view of one guide pin insertion cylinder of the rear cylinder unit and FIG. 9B is a rear view of the one guide pin insertion cylinder.
Figure 9B:
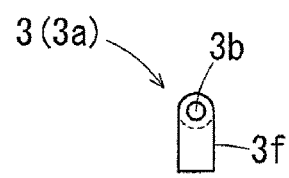
Figure 10A:
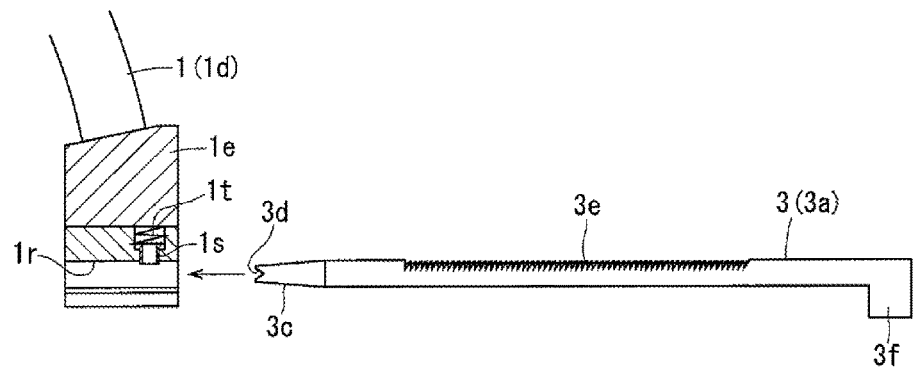
FIGS. 10A-10C illustrate how each guide pin insertion cylinder is inserted into an insertion hole provided at the rear end of the frame.
Figure 10B:
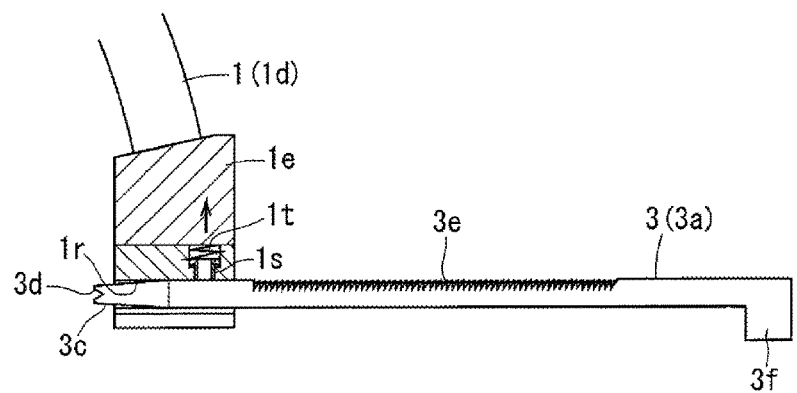
Figure 10C:
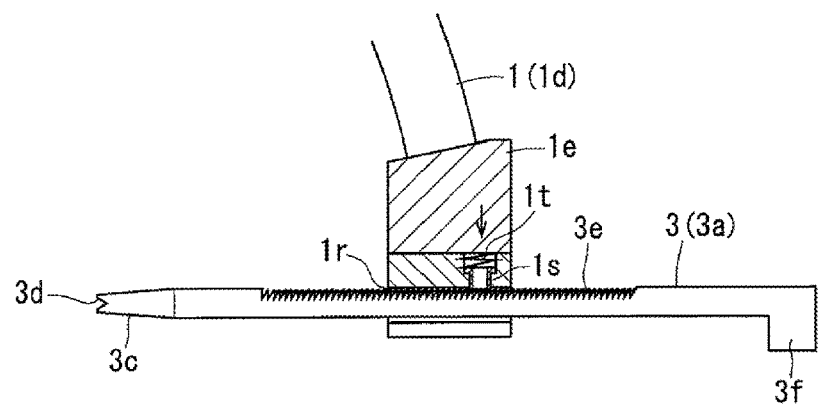
Figure 11A:
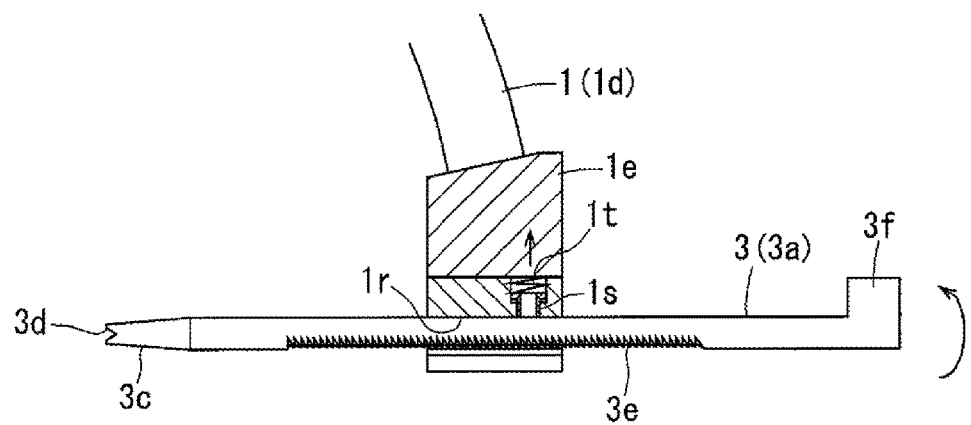
FIGS. 11A and 11B illustrate how each guide pin insertion cylinder is pulled out of the rear-end insertion hole of the frame.
Figure 11B:
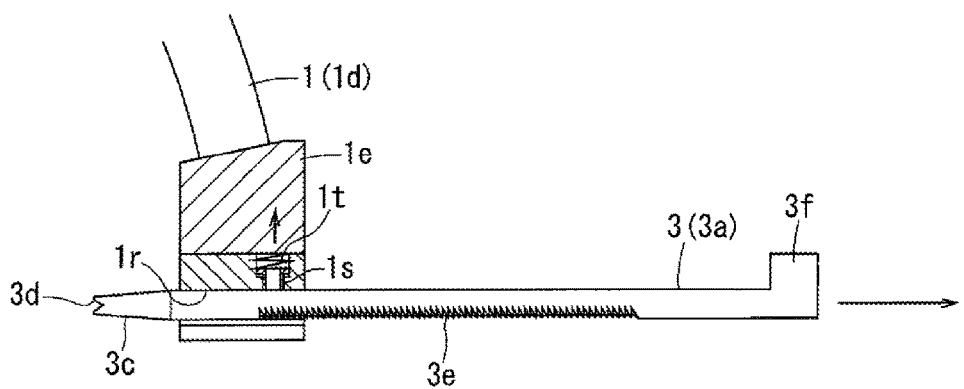

FIG. 1 is a side view of a guide pin piercing jig according to an embodiment of the invention, FIG. 2 is a side view showing a state that guide pins for hollow drills are inserted in guide pin insertion cylinders of a rear cylinder unit of the guide pin piercing jig, FIG. 3 is a side view of a frame of the guide pin piercing jig, FIG. 4 is a rear view of the frame, FIG. 5 shows an end view of cutting FIG. 3 along the line A-A, FIG. 6 shows an end view of cutting FIG. 3 along the line B-B, FIG. 7 shows the frame as viewed from above and the front side, FIG. 8A is a plan view of a front cylinder unit, FIG. 8B is a side view of the front cylinder unit, FIG. 8C is a front view of the front cylinder unit, FIG. 8D is a sectional view taken along the line C-C in FIG. 8B, FIG. 9A is a side view one guide pin insertion cylinder of the rear cylinder unit, FIG. 9B is a rear view of the one guide pin insertion cylinder, FIG. 10A, 10B, and 10C illustrate how the guide pin insertion cylinders are inserted into respective insertion holes of a rear end portion of the frame, and FIGS. 11A and 11B illustrate how the guide pin insertion cylinders are pulled out of the respective insertion holes of the rear end portion of the frame.

As described later, the guide pin piercing jig 10 shown in FIGS. 1 and 2 is to be used for piercing a thighbone bottom portion of the knee joint with guide pins for hollow drills in such a manner that their positions and direction are determined correctly according to the intension of a doctor in boring, in the thighbone bottom portion, by the hollow drills, bone tunnels that are necessary to transplant a tendon acquired from another part in the knee joint in reconstruction of a torn anterior cruciate ligament (ACL). The guide pin piercing jig 10 includes a frame 1 which is curved approximately in a semi-circular shape, a front cylinder unit 2 which is attached to a front end portion of the frame 1 in a detachable manner, and a rear cylinder unit 3 which is attached to a rear end portion of the frame 1 in a detachable and slidable manner. Each of the frame 1, the front cylinder unit 2, and the rear cylinder unit 3 is made of a metal such as titanium or stainless steel.

Figure 14:
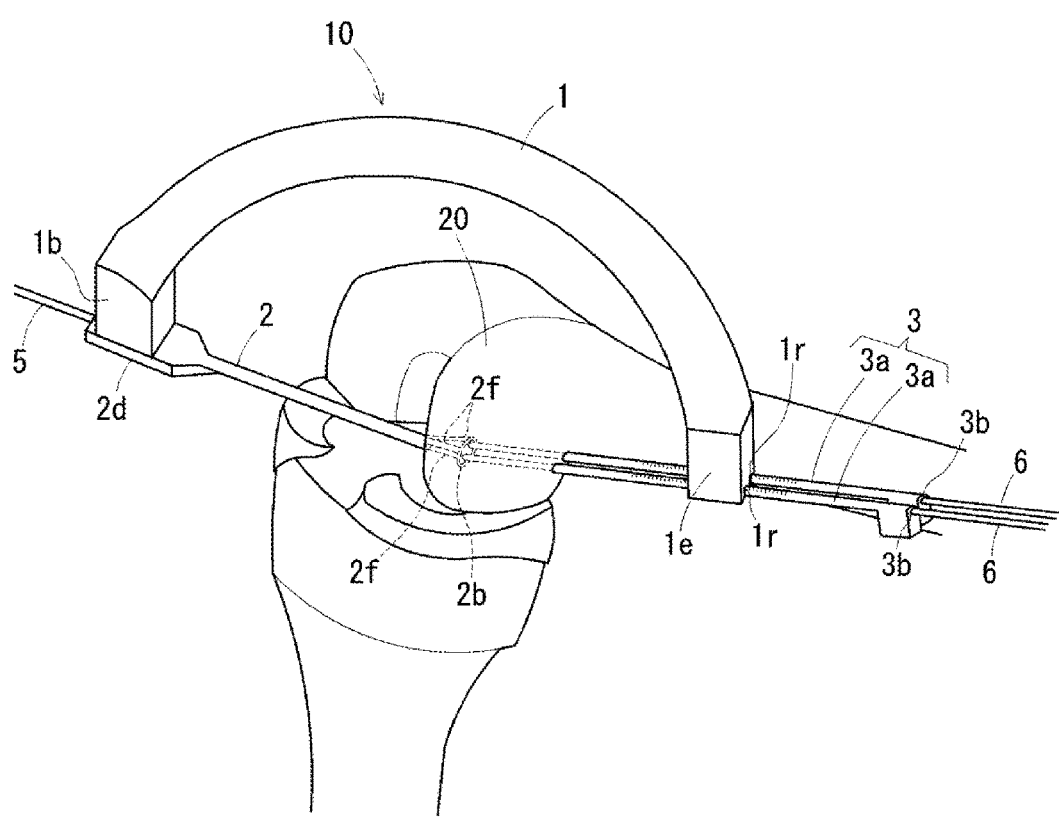
FIG. 14 illustrates an example manner of use of the guide pin piercing jig and shows a state that guide pins have been inserted, from behind, into the respective guide pin insertion cylinders which are fixed tentatively to the back surface of the thighbone bottom portion and have pierced the thighbone bottom portion until reaching the boring aiming portion of the front cylinder unit.

Although in FIGS. 1 and 2 only one guide pin insertion cylinder 3a on one side is shown as the rear cylinder unit 3, actually the rear cylinder unit 3 has two parallel guide pin insertion cylinders 3a, 3a as shown in FIG. 14.

As shown in FIGS. 3 and 4, the frame 1 which is curved approximately in semi-circular form includes a curved circular pipe 1a, a front cylinder unit attachment portion 1b which is connected to the front end of the circular pipe 1a, a curved sheath 1c which is connected to the rear end of the circular pipe 1a, a curved plate 1d which is inserted in the curved sheath 1c in a slidable manner, a rear cylinder unit attachment portion 1e which is connected to the rear end of the curved plate 1d, and a knob 1f for locking the curved plate 1d to stop its slide. The center lines of the curved circular pipe 1a, the curved sheath 1c, and the curved plate 1d have the same radius of curvature. So that the frame 1 can stride over the knee joint, the radius of curvature is set to 50 to 300 mm, preferably to 80 to 220 mm, even preferably to 100 to 180 mm As shown in FIGS. 5 and 6, a screw shaft 1g of the knob if is threadedly engaged with a screw hole 1h which is formed through a side wall (located on the side opposite to a side wall in which a slit is formed) of the curved sheath 1c. When the screw shaft 1g is screwed in by rotating the knob 1f with fingers, a tip contact piece 1i of the screw shaft 1g comes into pressure contact with the bottom surface of a shallow recess 1j that is formed in a side surface of the curved plate 1d, whereby the curved plate 1d is fixed, that is, made incapable of sliding. Therefore, the entire arc length of the frame 1 can be adjusted by sliding the curved plate 1d in the curved sheath 1c along the circular arc with the knob if loosened and then rotating the knob if to fix the curved plate 1d so as to be incapable of sliding. In this manner, the angle θ formed by the center axis CL2 of the front cylinder unit 2 and the center axis CL3 of the rear cylinder unit 3 (guide pin insertion cylinders 3a) can be set to an optimum angle as shown in FIG. 1.

The attachment portion 1b which is a front end portion of the frame 1 (i.e., is connected to the front end of the circular pipe 1a) serves to attach the front cylinder unit 2 to the frame 1 in a detachable manner. As shown in FIG. 7, a pair of nipping pieces 1m, 1m having respective lock nails 1k at the bottom ends are attached swingably to the body of the attachment portion 1b on two respective sides via respective support shafts 1n, 1n. A compression spring 1p is stretched between top end portions of the respective nipping pieces 1m, 1m. Since the bottom lock nails 1k, 1k of the respective nipping pieces 1m are deviated from each other in the front-rear direction as shown in FIG. 3, they can hold and attach the front cylinder unit 2 stably. The bottom surface of the attachment portion 1b is provided with two positioning projections 1q, 1q which determine an attachment position of the front cylinder unit 2 so that the two positioning projections 1q, 1q are disposed so as to correspond to two diagonal ones of four fitting holes 2h (see FIG. 8A) of the front cylinder unit 2.

As shown in FIGS. 8A, 8B, 8C, and 8D, the front cylinder unit 2 which is attached to the bottom surface of the attachment portion 1b is provided with a straight cylinder 2a, a boring aiming portion 2b and positioning projections 2c which are provided at the tip of the cylinder 2a, and a flat cylinder base portion 2d which is provided in the rear of the cylinder 2a. A straight cylinder hole 2e penetrates through the front cylinder unit 2 from the tip of the cylinder 2a to the tail of the cylinder base portion 2d along the center axis CL2.

The boring aiming portion 2b is a ring-shaped body having an elliptical opening as shown in FIG. 8C and is fixed to the tip of the cylinder 2a by three thin support pieces 2f as shown in FIGS. 8A and 8B. The reason why the boring aiming portion 2b is made a ring-shaped body having an elliptical opening which approximately coincides with an opening shape (rectangular or elliptical as mentioned above) of a bone tunnel to be formed finally is to allow a doctor to image such a bone tunnel. The reason why the boring aiming portion 2b which is a ring-shaped body is fixed to the tip of the cylinder 2a by the thin support pieces 2f is to make it possible to check, through the gaps between the thin support pieces 2f, using a fiber scope or the like, whether or not the tips of guide pins have reached the opening of the boring aiming portion 2b in a guide pins piercing attempt, as described later.

As shown in FIG. 8A, a ring-shaped tip surface 2g of the boring aiming portion 2b is inclined so as to form an angle of 70° to 80°, preferably 75°, with the center axis CL2 of the front cylinder unit 2 and is perpendicular to the paper surface of FIG. 8A. That is, with the x axis, y axis, and z axis defined in FIG. 8A as the axis CL2, the axis perpendicular to the axis CL2 in the paper surface, and the axis perpendicular to the paper surface, respectively, the tip surface 2g is parallel with the Z axis whereas being inclined by 10° to 20° from the y axis.

Therefore, it is possible to insert the front cylinder unit 2 into the knee joint from the front side and bring, stably, the boring aiming portion 2b into contact with a curved slant surface of a portion, to which to bore a bone tunnel, of a thighbone bottom portion. When the tip surface of the boring aiming portion 2b is brought into contact with a curved slant surface of a thighbone bottom portion and pushed strongly, the pair of sharp positioning projections 2c, 2c which project from the tip surface of the boring aiming portion 2b stick into the curved slant surface of the thighbone bottom portion, whereby the boring aiming portion 2b is positioned and fixed temporarily.

As shown in FIGS. 8A and 8D, the four fitting holes 2h into which the two positioning projections 1q, 1q which project from the bottom surface of the attachment portion 1b of the frame 1 can be fitted in a detachable manner are formed through the flat cylinder base portion 2d of the front cylinder unit 2 so as to be spaced from each other in the front-rear and left-right directions. The reason why the four fitting holes 2h are formed is to allow the two positioning projections 1q, 1q to be fitted into the two respective diagonal ones of the four fitting holes 2h when the flat cylinder base portion 2d of the front cylinder unit 2 is attached to the attachment portion 1b after being vertically flipped by 180° about the center axis CL2.

Since the front cylinder unit 2 can be attached to the attachment portion 1b even when vertically flipped by 180° about the center axis CL2 as described above, the tip boring aiming portion 2b after flipping is be made left/right symmetrical with that before the flipping. Therefore, the tip surface 2g, capable of being inclined to either of two opposite directions, of the boring aiming portion 2b can be applied stably to a curved slant surface, where to form a bone tunnel, of the thighbone of whichever of the left and right legs. Curved surfaces of portions, where to form a bone tunnel, of thighbone bottom portions of the left knee joint and the right knee joint are inclined to opposite directions. Therefore, the tip face 2g of the boring aiming portion 2b can be applied stably to the curved slant surfaces of the thighbone bottom portions of both of the left knee joint and the right knee joint by inclining it to opposite directions by vertically flipping the front cylinder unit 2 by 180°.

FIGS. 12-20 illustrate how a bone tunnel is bored through a left thighbone bottom portion. The rear cylinder unit 3 is located behind and on the left of the thighbone bottom portion, whereby a space for an operation is secured to facilitate the operation. To bore a bone tunnel through a right thighbone bottom portion, an operation is performed with the rear cylinder unit 3 located behind and on the right of it, that is at the position left-right symmetrical to the human body.

As shown in FIG. 8C, in the flat cylinder base portion 2d of the front cylinder unit 2, one surface (top surface) 2j and the opposite surface (bottom surface) 2k are inclined surfaces that are inclined by 2° to 5°, preferably 3.5°, to opposite directions except for a rear-end thick portion 2i.

This is to incline the front cylinder unit 2 by the above angle when the cylinder base portion 2d is brought into contact with and attached to the bottom surface of the attachment portion 1b, to thereby allow the tips of two guide pins 6, 6 to go into the opening of the boring aiming portion 2b reliably when the guide pins 6, 6 have passed through the respective guide pin insertion cylinders 3a, 3a and pierced the bone as described 1ater.

Since the top and bottom surfaces 2j and 2k of the cylinder base portion 2d are inclined by 3.5° to opposite directions, where the center axis CL2 of the front cylinder unit 2 and the center axis CL3 of the rear cylinder unit 3 cross each other at 150° to 160°, the tips of two guide pins 6, 6 that have passed through the respective guide pin insertion cylinders 3a, 3a of the rear cylinder unit 3 and pierced the bone go into the opening of the boring aiming portion 2b.

As shown in FIGS. 8A and 8B, each of two side portions of the top and bottom surfaces of the flat cylinder base portion 2d is formed with lock counterpart portions 2m and 2n on which the lock nails 1k, 1k of the nipping pieces 1m, 1m of the front-end attachment portion 1b of the frame 1 can be locked without play when the front cylinder unit 2 is attached to the attachment portion 1b irrespective of whether the front cylinder unit 2 is flipped upside down or not. The lock counterpart portions 2m and 2n are formed by cutting each of two side portions of the top and bottom surfaces of the cylinder base portion 2d obliquely and their cutting depths and inclination angles are changed so that the lock nails 1k, 1k of the nipping pieces 1m, 1m can be locked reliably without play.

The front cylinder unit 2 can easily be attached to the front-end attachment portion 1bof the frame 1 in the following manner. First, top portions of the pair of nipping pieces lm, 1m of the attachment portion 1b are pushed from both sides against the resilient force of the compression spring 1p, whereby the bottom-end lock nails 1k, 1k of the nipping pieces lm are opened to both sides. In this state, the positioning projections 1q, 1q of the attachment portion 1b are fitted into the respective fitting holes 2h, 2h of the cylinder base portion 2d of the front cylinder unit 2. Then the bottom ends of the nipping portions 1m, 1m are rotated inward by the resilient force of the compression spring 1p, whereby the lock nails 1k, 1k are locked on the lock counterpart portions 2m and 2n of the cylinder base portion 2d. The attaching work is thus completed. To remove the front cylinder unit 2, the lock nails 1k, 1kare unlocked by pushing top portions of the nipping pieces 1m, 1m of the attachment portion lb from both sides and the positioning projections 1q, 1q of the attachment portion 1b are pulled out of the respective fitting holes 2h, 2h of the cylinder base portion 2d.

When the front cylinder unit 2 is attached to the front-end attachment portion 1b of the frame 1 in the above manner, as shown in FIG. 1 the front cylinder unit 2 is directed to the center the imaginary circle of the circular-arc-shaped frame 1 and extends straightly from the attachment portion 1b toward the center of the circular arc and the boring aiming portion 2b of the tip of the front cylinder unit 2 is located near the center of the circular arc of the frame 1.

The front cylinder unit 2 which is attached to the front end of frame 1 and the rear cylinder unit 3 which is attached to the rear end of the frame 1 extend straightly so that their center lines CL2 and CL3 face to and cross each other. Since the boring aiming portion 2b which is provided at the tip of the front cylinder unit 2 is located at the crossing point, one can suppose, using the boring aiming portion 2b, where openings will be formed on the side of the front cylinder unit 2 by piercing from the side of the rear cylinder unit 3. Since portions of a living body bone that are reached from the front cylinder unit 2 and the rear cylinder unit 3 are located on extensions of the axes of the front cylinder unit 2 and the rear cylinder unit 3, respectively, the area of a part to be incised of the living body can be made small, which is preferable because of a lighter load on the living body.

Although in the embodiment the frame 1 has a circular arc shape, all or part of the frame excluding the curved sheath 1c and the curved plate 1d which is inserted in the curved sheath 1c or all or part of a frame having neither the sheath 1c nor the curved plate 1d need not always have a circular arc shape.

As shown in FIG. 14, the rear cylinder unit 3 which is attached to the rear-end attachment portion 1e of the frame 1 has the plural (two) parallel guide pin insertion cylinders 3a. As shown in FIGS. 9A and 9B, a straight cylinder hole 3b through which to insert a guide pin is formed through each guide pin insertion cylinder 3a along the center axis CL3. Whereas the guide pin insertion cylinder 3a has a straight cylinder shape as a whole, a tip neighborhood portion 3c is tapered and its tip is formed with a sharp opening 3d having cuts as a tentative fixing unit. A top portion, having a width that is approximately equal to ¼ of the circumference, of the circumferential surface of a central portion of each guide pin insertion cylinder 3a excluding its portions adjacent to its front end and rear end is formed with a sawtooth-shaped ratchet portion 3e which extends continuously in the longitudinal direction of the guide pin insertion cylinder 3a. Furthermore, a projection piece 3f projects from a rear end portion of each guide pin insertion cylinder 3a to the side opposite to the ratchet portion 3e (i.e., downward).

On the other hand, as shown in FIGS. 1-4 and 10A-10C, two insertion holes 1r, 1r (insertion holes each of which is formed with a slit at the bottom) for slidable attachment of the respective guide pin insertion cylinders 3a are formed through the rear-end attachment portion be of the frame 1 parallel with each other in the centripetal direction of the frame 1. An engagement projection 1s, 1s for preventing a rearward slide of the corresponding guide pin insertion cylinder 3a by engaging with its ratchet portion 3e projects slightly, being pushed by a compression spring 1t, 1t from behind (above), through a top portion of the inner surface that defines each insertion hole 1r, 1r.

Therefore, when each guide pin insertion cylinder 3a is inserted into the corresponding insertion hole 1r from behind the rear-end attachment portion be of the frame 1 as shown in FIG. 10A, the engagement projection 1s is pushed up by the tapered surface of the tip portion 3c of the guide pin insertion cylinder 3a as shown in FIG. 10B. When the guide pin insertion cylinder 3a is inserted further, as shown in FIG. 10C the engagement projection is is engaged with the ratchet portion 3e being pushed by the compression spring 1t and thereby prevents a rearward slide of the guide pin insertion cylinder 3a while allowing it to slide forward.

As shown in FIG. 11A, the engagement between the engagement projection is and the ratchet portion 3e of the guide pin insertion cylinder 3a is canceled by vertically flipping the guide pin insertion cylinder 3a by 180° by rotating the projection piece 3f. Therefore, the guide pin insertion cylinder 3a can be taken out of the rear-end attachment portion be of the frame 1 by sliding the guide pin insertion cylinder 3a rearward in the above state as shown in FIG. 11B.

When the guide pin insertion cylinders 3a are inserted into the respective insertion holes 1r of the attachment portion 1e of the frame 1 in the above-described manner, as shown in FIG. 1 the guide pin insertion cylinders 3a are attached slidably so as to be directed to the centripetal direction of the frame 1. And the tip openings 3d of the guide pin insertion cylinders 3a reach close to the tip boring aiming portion 2b of the front cylinder unit 2 and the center axis CL3 of the guide pin insertion cylinders 3a passes through the tip boring aiming portion 2b of the front cylinder unit 2. Therefore, when guide pins 6 for hollow drills are inserted into cylinder holes of the guide pin insertion cylinders 3a, respectively, shown in FIG. 2, the tips of the guide pins 6 go into the boring aiming portion 2b of the front cylinder unit 2.

The crossing angle θ between the center axis CL2 of the front cylinder unit 2 and the center axis CL3 of the guide pin insertion cylinders 3a need to be larger than 90° and smaller than 180°. In the case of piercing a thighbone bottom portion of the knee joint with guide pins 6 for hollow drills to bore a bone tunnel for tendon transplantation through it as in the embodiment, it is desirable that the crossing angle θ be set to 145° to 175°, most preferably to 150° to 160°. When the crossing angle θ is set in such a range, the guide pins can pierce the thighbone bottom portion of the knee joint in a direction that is in a proper range.

As described above, the crossing angle θ between the center axis CL2 of the front cylinder unit 2 and the center axis CL3 of the guide pin insertion cylinders 3a can be adjusted easily by increasing or decreasing the entire circular arc length of the frame 1 to set the angle θ to a desired angle by sliding the curved plate 1d in the circular arc extending direction in the curved sheath 1c in a state that the knob 1f is loosened and then fixing the curved plate 1d so as to be unslidable by bringing the contact piece 1i into contact with the recess 1j of the curved plate 1d by rotating the knob 1f.

Next, a method for using the above-described guide pin piercing jig and a method for boring a bone tunnel in ACL reconstruction of the knee joint will be described with reference to FIGS. 12 to 21D.

FIGS. 12-20 schematically show the shape of the guide pin piercing jig, the shape of a thighbone bottom portion of the knee joint, the shape of a shinbone top portion, etc.

Figure 12:
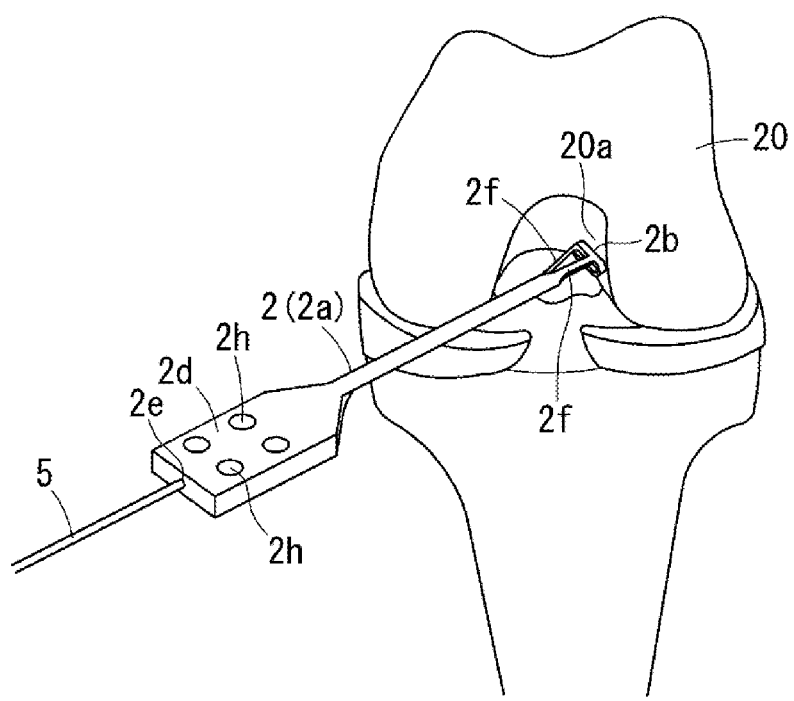
FIG. 12 illustrates an example manner of use of the guide pin piercing jig and shows a state that a boring aiming portion of the front cylinder unit is applied to a curved slant surface of a thighbone bottom portion of the knee joint and the front cylinder unit is fixed by a fixing pin.

As shown in FIG. 12, the front cylinder unit 2 is inserted into the knee joint from the front side and the boring aiming portion 2b is applied to a recessed, curved slant surface 20a of a portion, to which to bore a bone tunnel, of a thighbone bottom portion 20 and pressed against it strongly, whereby the tip positioning projections 2c (unseen in FIG. 12) are stuck into the curved slant surface 20a of the thighbone bottom portion 20 and the boring aiming portion 2b is thereby positioned and fixed temporarily. Then, a tentative fixing pin 5 is inserted through the cylinder hole 2e of the front cylinder unit 2 and its tip portion is stuck into the thighbone bottom portion 20 through its curved slant surface 20a by about 15 mm The front cylinder unit 2 is fixed tentatively by the tentative fixing pin 5.

Since as mentioned above the boring aiming portion 2b is a ring-shaped body having an elliptical opening which approximately coincides with an opening shape (rectangular or elliptical) of a bone tunnel to be formed finally, a doctor can perform work of positioning the boring aiming portion 2b easily by applying the boring aiming portion 2b to a proper portion of the curved slant surface 20a of the thighbone bottom portion 20 while imaging the shape of a bone tunnel to be formed finally.

Figure 13:
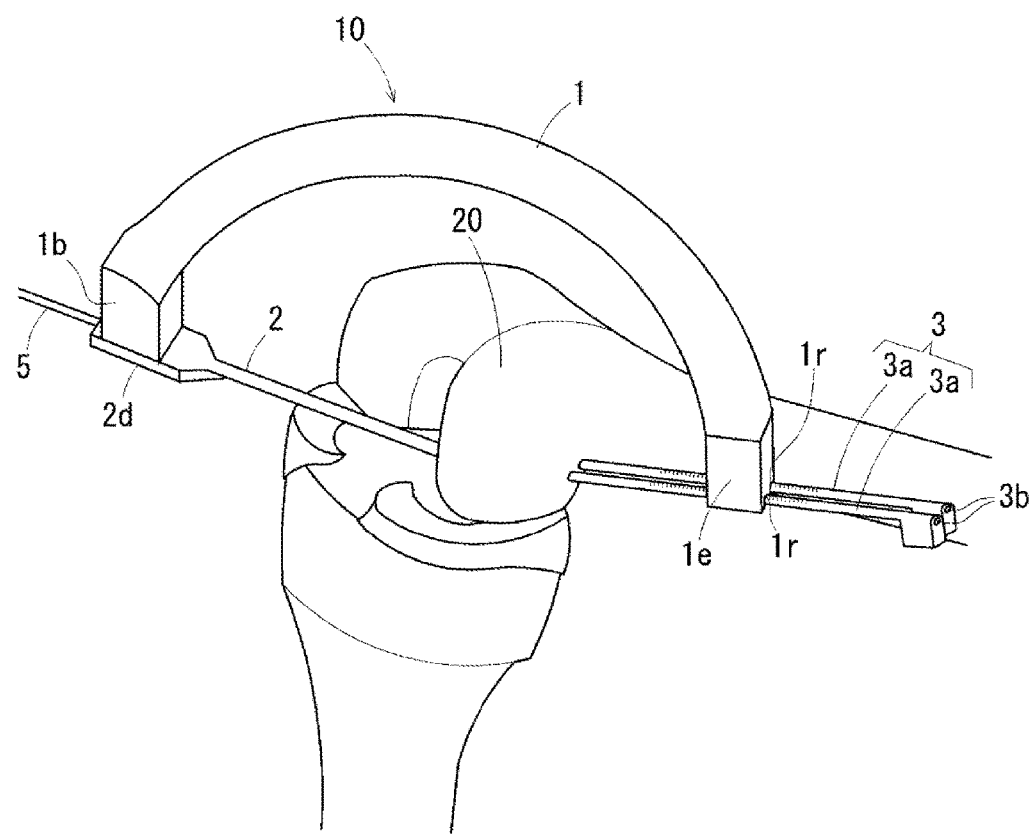
FIG. 13 illustrates an example manner of use of the guide pin piercing jig and shows a state that the front cylinder unit is attached to the frame and the plural guide pin insertion cylinders of the rear cylinder unit have been fixed tentatively to a back surface of the thighbone bottom portion by sliding them toward the tip of the front cylinder unit.

After completion of the work of tentatively fixing the front cylinder unit 2, as shown in FIG. 13 the cylinder base portion 2d of the front cylinder unit 2 is attached to the front-end attachment portion 1b of the frame 1 of the guide pin piercing jig 10 in a detachable manner. Then the two guide pin insertion cylinders 3a of the rear cylinder unit 3 are inserted into the respective insertion holes 1r of the rear-end attachment portion 1e of the frame 1. And the guide pin insertion cylinders 3a, 3a are attached in a state that their tip sharp openings 3c (unseen in FIG. 13) are stuck into the thighbone bottom portion 20 from obliquely behind and thereby fixed tentatively.

How to attach the cylinder base portion 2d of the front cylinder unit 2 to the attachment portion 1b of the frame 1 has already been described above and hence is not described here.

As described above, the guide pin insertion cylinders 3a, 3a are attached so as to be incapable of removal because the engagement projections 1s, is which are exposed through the top portions of the inner surfaces of the insertion holes 1r, 1r are engaged with the respective ratchets 3e, 3e.

When the front cylinder unit 2 is attached to the front-end attachment portion 1b of the frame 1 and the two guide pin insertion cylinders 3a, 3a of the rear cylinder unit 3 are attached to the rear-end attachment portion 1e of the frame 1, the frame 1 which is curved in circular arc form strides over the thighbone bottom portion 20 of the knee joint. As shown in FIG. 1, the center axis CL3 of the guide pin insertion cylinders 3a passes through the tip boring aiming portion 2b of the front cylinder unit 2.

It is desirable that the crossing angle θ between the center axis CL2 of the front cylinder unit 2 and the center axis CL3 of the guide pin insertion cylinders 3a be set in advance in a range of 150° to 160° by adjusting the circular arc length of the frame 1 so that the guide pin insertion cylinders 3a which are located obliquely behind the thighbone bottom portion 20 are directed to the boring aiming portion 2b of the front cylinder unit 2 at a proper angle. How to adjust the circular arc length of the frame 1 has already been described above and hence is not described here.

Setting of the angle θ (i.e., adjustment of the circular arc length of the frame 1) may be made after attachment of the guide pin insertion cylinders 3a.

Subsequently, as shown in FIG. 14, guide pins 6, 6 for hollow drills are inserted into the cylinder holes 3b, 3b of the guide pin insertion cylinders 3a, 3a and caused to pierce the thighbone bottom portion 20 until the tips of the guide pins 6 go into the opening of the boring aiming portion 2b of the front cylinder unit 2. The tips of the guide pins 6, 6 are sharp like the tip of a drill, and the guide pins 6, 6 can pierce the thighbone bottom portion 20 relatively easily when rotated. Whether or not the guide pins 6, 6 have penetrated through the thighbone bottom portion 20 and their tips have gone into the opening of the boring aiming portion 2b of the front cylinder unit 2 may be checked through the gaps between the thin support pieces 2f of the boring aiming portion 2b by inserting a fiber scope into the knee joint. In the example of FIG. 14, observation is possible with a fiber scope that is inserted from the right side of the front cylinder unit 2. Since no support piece 2f exists on the right side, a large gap (opening) is secured there; no part of the field of view of the fiber scope is lost and a check is thus facilitated.

In this operation, all the incised part to the living body is only four small openings for insertion of the front cylinder unit, the rear cylinder unit, the fiber scope, and a pipe to be used for filling the operation part with physiological saline each of which generally assumes a rod shape. This operation method is superior because of formation of small incised part which means a lighter load on the living body.

After confirmation of entrance of the tips of the guide pins 6, 6 into the boring aiming portion 2b, the guide pin insertion cylinders 3a, 3a are pulled out of the respective insertion holes 1r, 1r of the rear-end attachment portion 1e of the frame 1 and then removed from the respective guide pins 6, 6. Subsequently, the frame 1 and the front cylinder unit 2 are separated from each other and removed from the knee joint and the tentative fixing pin 5 is also removed, as a result of which only the two guide pins 6, 6 are left as shown in FIG. 15 and the work of piercing the thighbone bottom portion 20 with the guide pins 6, 6 is completed.

How to pull the guide pin insertion cylinders 3a, 3a from the respective insertion holes 1r and how to separate the frame 1 and the front cylinder unit 2 from each other have already been described above and hence are not described here.

Figure 15:
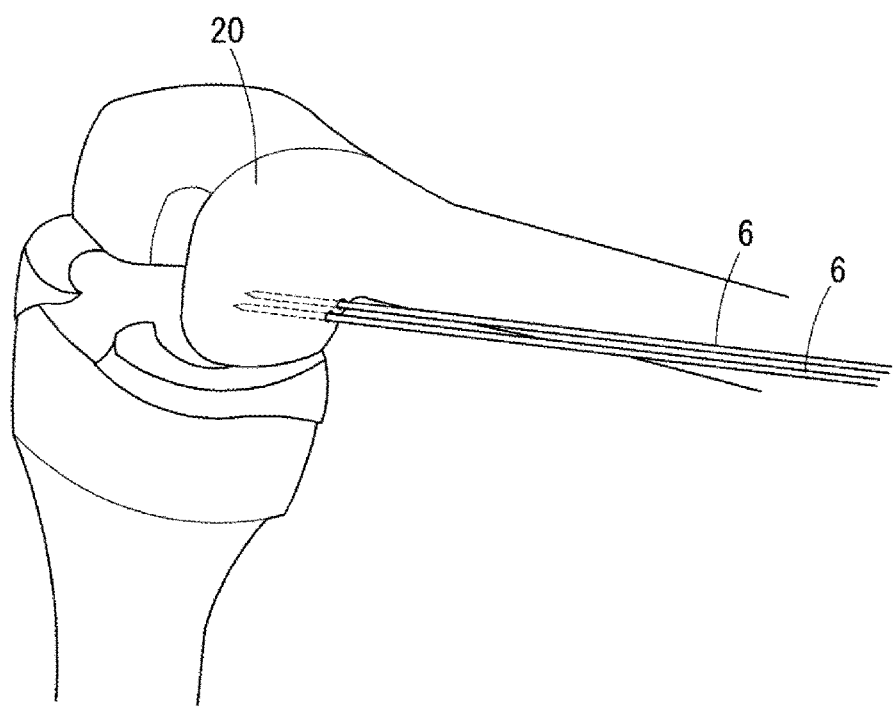
FIG. 15 illustrates an example manner of use of the guide pin piercing jig and shows a state that the plural guide pin insertion cylinders are pulled out and the frame and the front cylinder unit are removed.
Figure 16:
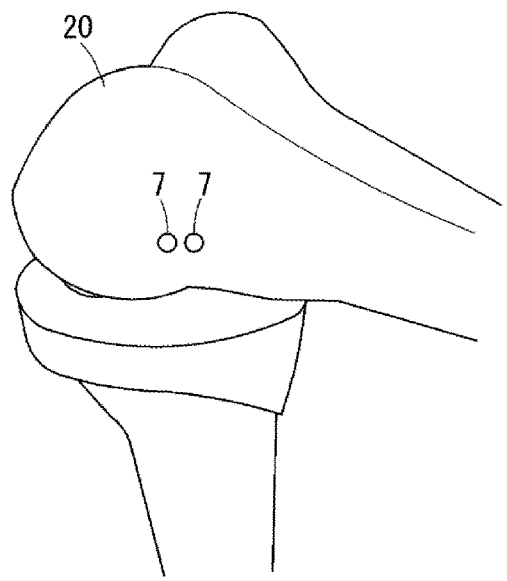
FIG. 16 is a perspective view showing the thighbone bottom portion of the knee joint in which plural bone tunnels have been bored from obliquely behind.

When the work of piercing the thighbone bottom portion 20 with the two guide pins 6, 6 has been performed in the above-described manner using the guide pin piercing jig 10 according to the present invention in the knee joint ACL reconstruction, as shown in FIG. 15 the two guide pins 6, 6 can pierce the thighbone bottom portion 20 in a proper direction from obliquely behind to a proper portion (i.e., a portion having, the recessed, curved slant surface 20a, of a thighbone bottom surface shown in FIG. 12) of the thighbone bottom portion 20 through which to bore a bone tunnel. Therefore, by boring the thighbone bottom portion 20 from obliquely behind along the guide pins 6, 6 by hollow drills (not shown), as shown in FIG. 16 two parallel circular bone tunnels 7, 7 can be formed which penetrate through the thighbone bottom portion 20 in a proper direction to a proper portion of the thighbone bottom portion 20.

Figure 17:
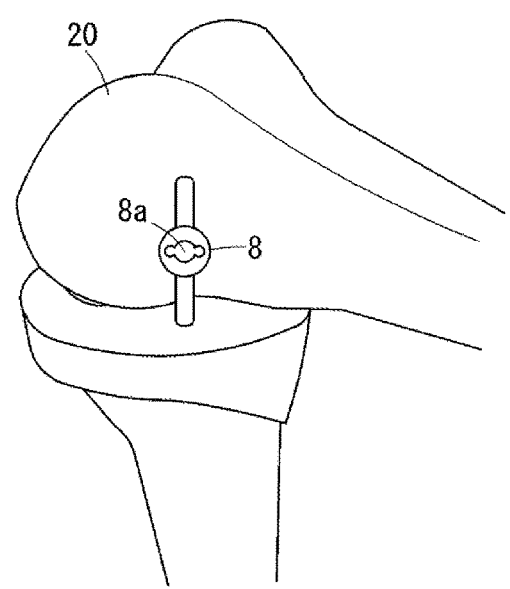
FIG. 17 is a perspective view showing a state that a center drill guide is inserted in the plural bone tunnels which are bored through the thighbone bottom portion of the knee joint.
Figure 18:
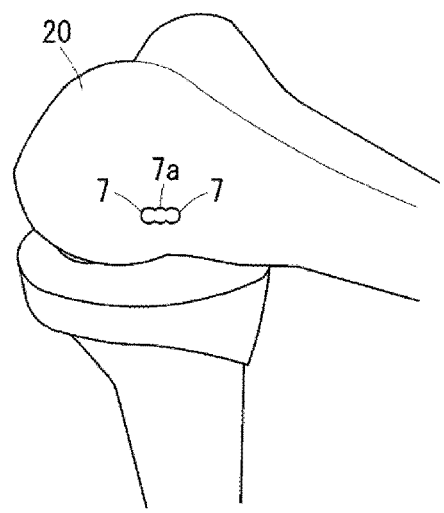
FIG. 18 is a perspective view showing the thighbone bottom portion of the knee joint in which the plural bone tunnels are connected to each other by boring a tunnel between them by a center drill.

In the next step, as shown in FIG. 17, a center drill guide 8 is inserted into the two bone tunnels 7, 7 (unseen in FIG. 17) and attached to the thighbone bottom portion 20 from behind. Then a center drill (not shown) is inserted into a guide hole 8a of the center drill guide 8, whereby as shown in FIG. 18 a link tunnel 7a is formed between the two circular bone tunnels 7, 7 to link them.

As shown in FIGS. 21A, 21B, 21C, and 21D, the center drill guide 8 includes a large-diameter base cylinder 8b having a guide hole 8a through which to insert a center drill, two small-diameter split cylinders 8c, 8c which project parallel with each other from the tip of the base cylinder 8b and are to be inserted into the bone tunnels 7, 7, and a generally T-shaped grip portion 8d which is connected to the rear end of the base cylinder 8b. The split cylinders 8c, 8c are formed, along their center lines, with pin insertion holes 8e, 8e into which to insert the guide pins 6, 6, respectively. The pin insertion holes 8e, 8e extend parallel with the guide hole 8a of the base cylinder 8b at its two respective sides. To prevent interference with the center drill to be inserted through the guide hole 8a of the base cylinder 8b, slits are formed in confronting cylinder wall portions between the split cylinders 8, 8c.

The thus-configured center drill guide 8 is used in the following manner. The two guide pins 6, 6 that are left inserted in the bone tunnels 7, 7 are inserted into the respective pin insertion holes 8e, 8e, the split cylinders 8c, 8c are guided to the respective bone tunnels 7, 7, and the split cylinders 8c, 8c are inserted into the bone tunnels 7, 7 and fixed by gripping the grip portion 8d with a hand. A link tunnel 7a is formed between the two bone tunnels 7, 7 so as to connect them by the center drill (not shown) that is inserted through the guide hole 8a. Then the split cylinders 8c, 8c are pulled out and the center drill guide 8 is removed.

Where the guide pins 6, 6 have been removed from the bone tunnels 7, 7, the tip split cylinders 8c, 8c are merely inserted into the respective bone tunnels 7, 7 and fixed by gripping the grip portion 8d. In this case, the pin insertion holes 8e, 8e are not necessary and hence need not always be formed.

Figure 19:
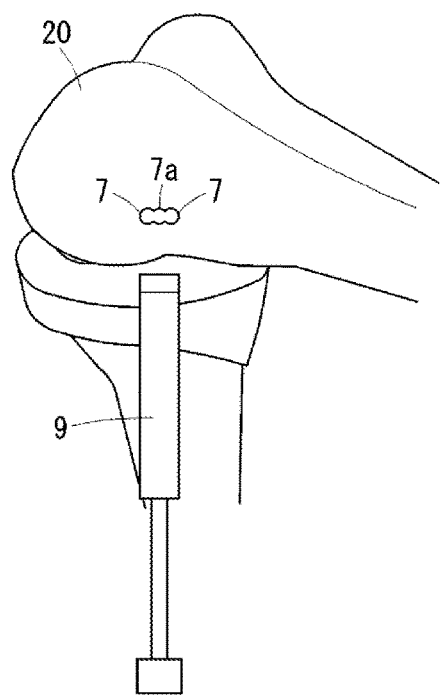
FIG. 19 is a perspective view showing how the continuous bone tunnel formed through the thighbone bottom portion of the knee joint are subjected to cutting with a chisel.
Figure 20:
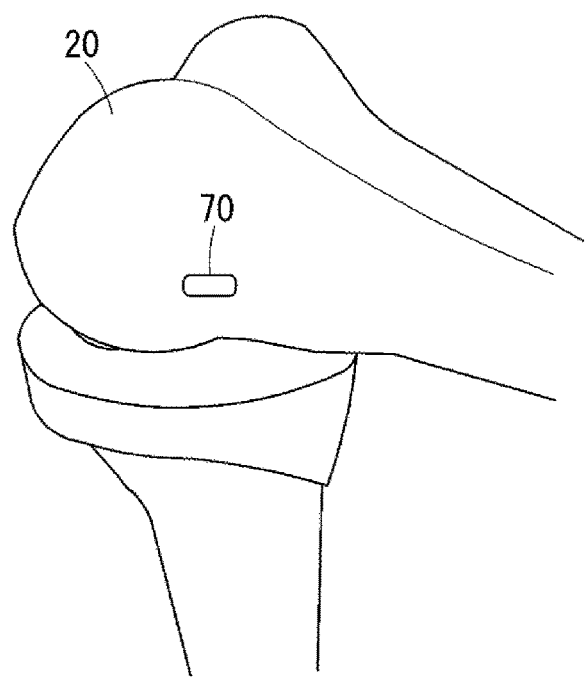
FIG. 20 is a perspective view showing the thighbone bottom portion of the knee joint through which a rectangular or elliptical bone tunnel is formed.
Figure 21A:
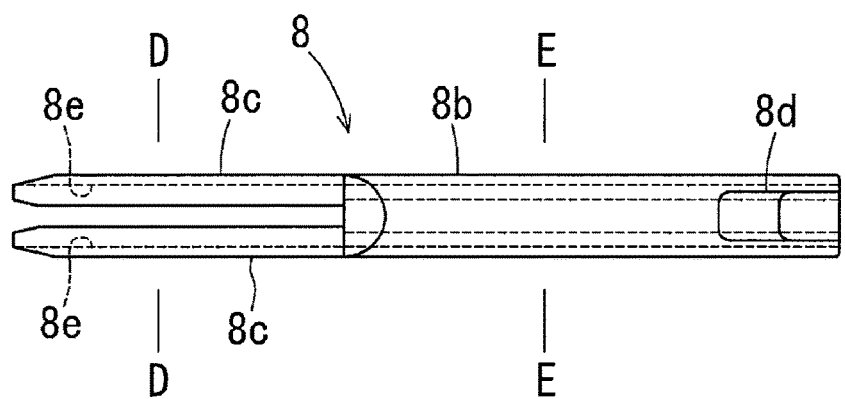
FIG. 21A is a plan view of the center drill guide.
Figure 21B:
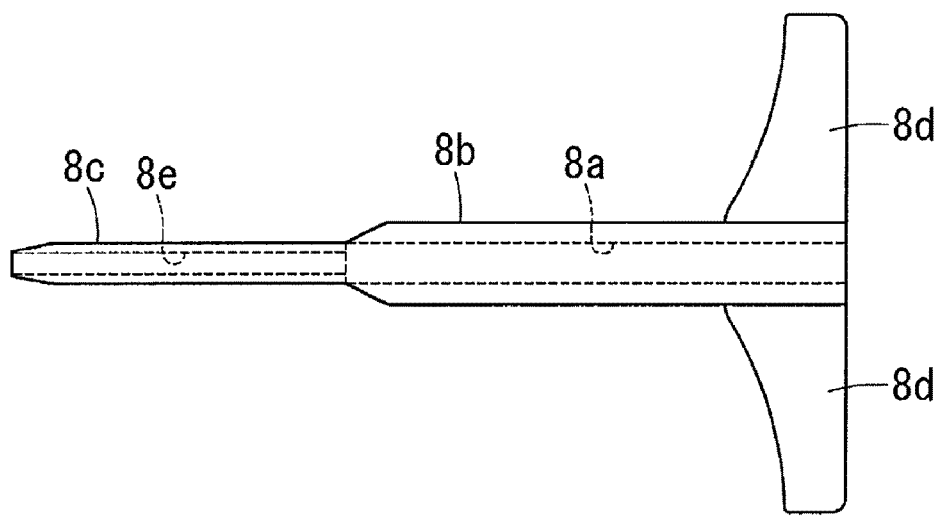
FIG. 21B is a side view of the center drill guide.
Figure 21C:
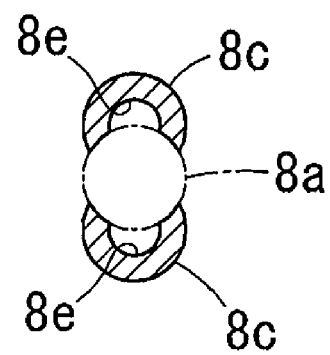
FIG. 21C is an enlarged end view of cutting FIG. 21A along the line D-D 21A.
Figure 21D:
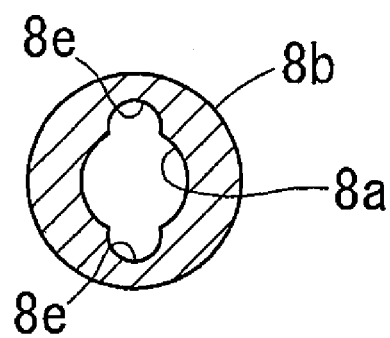
FIG. 21D is an enlarged end view of FIG. 21A along the line E-E.

After the bone tunnels 7, 7 have been connected to each other by the link bone tunnel 7a in the above-described manner, as shown in FIG. 19 the connected bone tunnel is subjected to cutting with a chisel 9 into a rectangular or elliptical shape or expansion with a dilator, whereby a rectangular or elliptical bone tunnel 70 is formed as shown in FIG. 20 which is different from a conventional circular bone tunnel and suitable for tendon transplantation. Since such a rectangular or elliptical bone tunnel 70 is formed, in the next step an approximately rectangular-parallelepiped-shaped bone piece, located at one end, of a transplantation tendon acquired from another part can be inserted into the bone tunnel 70 stably. And the bone piece, at the one end, of the transplantation tendon can be fixed strongly by screwing fixing screws (e.g., made of a polymer that is dissolved in and absorbed by a living body and having no screw head) through the bone piece and the inner surface of the bone tunnel 70.

A bone piece, at the other end, of the transplantation tendon is inserted into a bone tunnel that is bored through a shinbone top portion of the knee joint and fixed to the bone by screwing fixing screws through the bone piece and the inner surface of the bone tunnel.

Next, a guide pin piercing jig according to another embodiment of the invention will be described with reference to FIGS. 22-25B.

Figure 22:
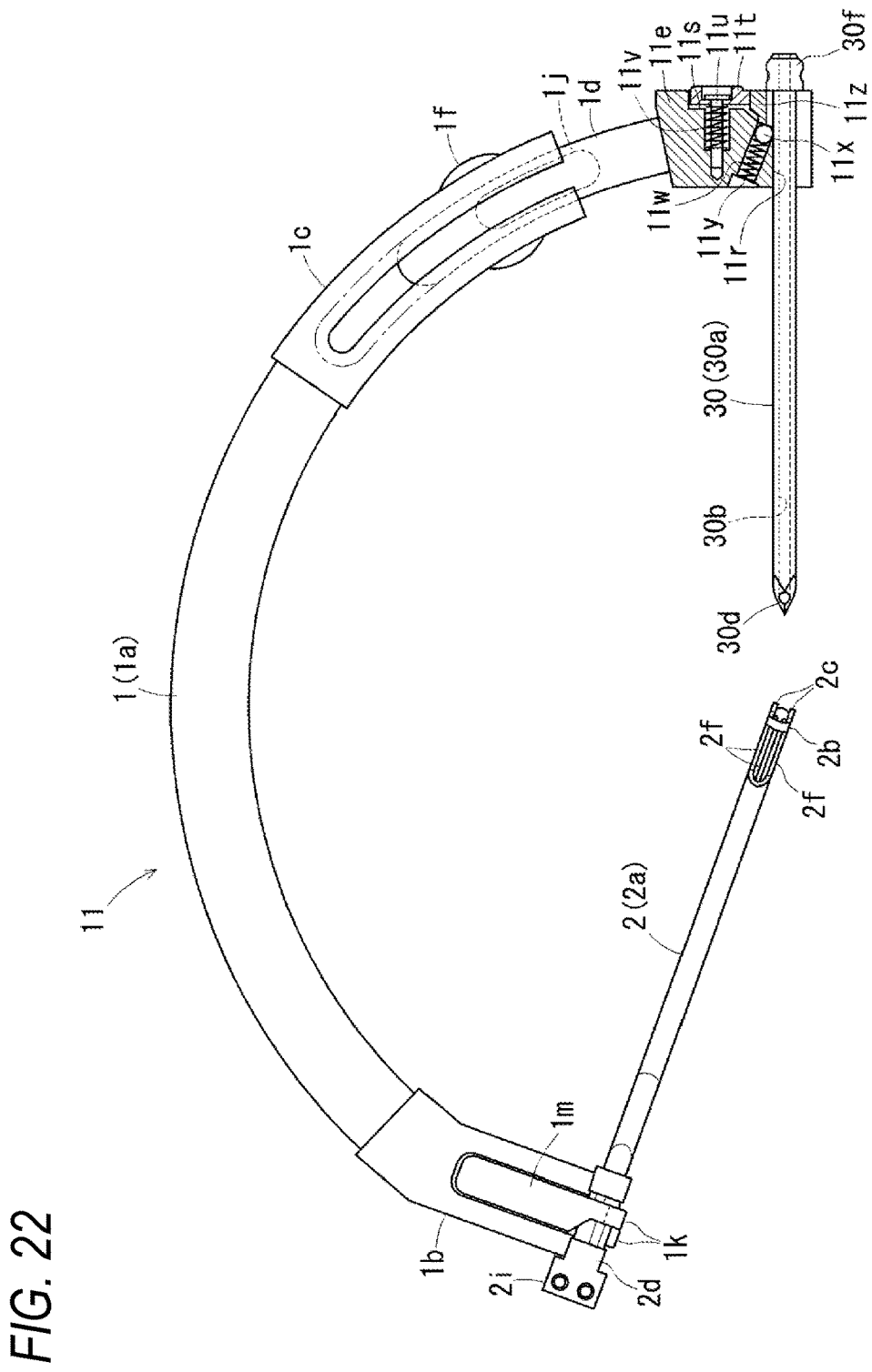
FIG. 22 is a side view of a guide pin piercing jig according to another embodiment of the invention.
Figure 23:
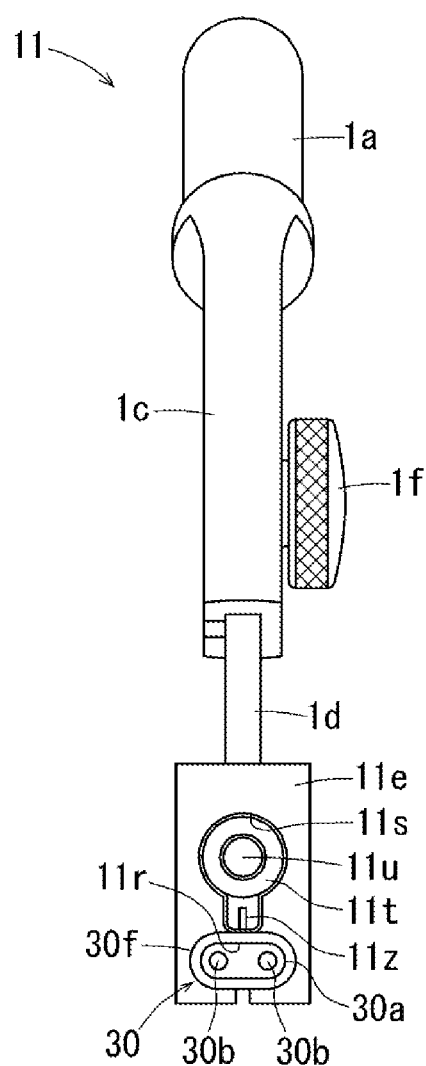
FIG. 23 is a rear view of the guide pin piercing jig.
Figure 24A:
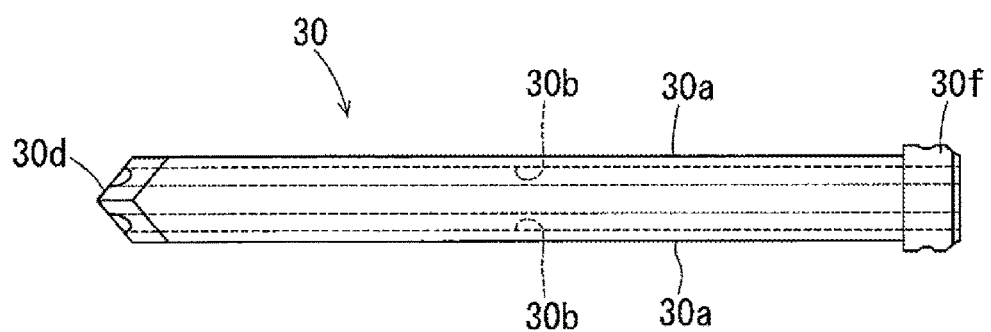
FIGS. 24A and 24B are a plan view and a side view, respectively, of another example of plural guide pin insertion cylinders of a rear cylinder unit.
Figure 24B:
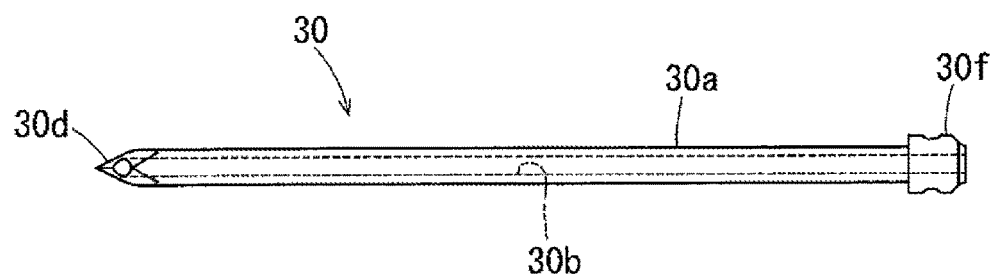
Figure 25A:
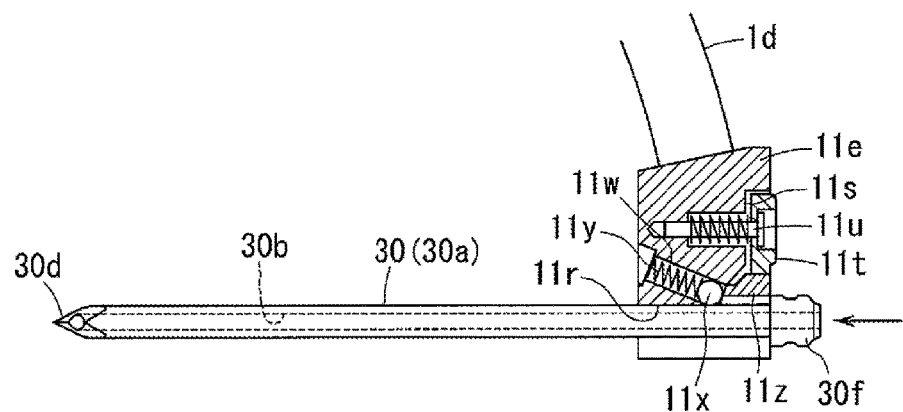
FIGS. 25A and 25B are sectional views of a rear end portion of a frame of the guide pin piercing jig that is holding the plural guide pin insertion cylinders of a rear cylinder unit of the rear cylinder unit in a slidable manner.
Figure 25B:
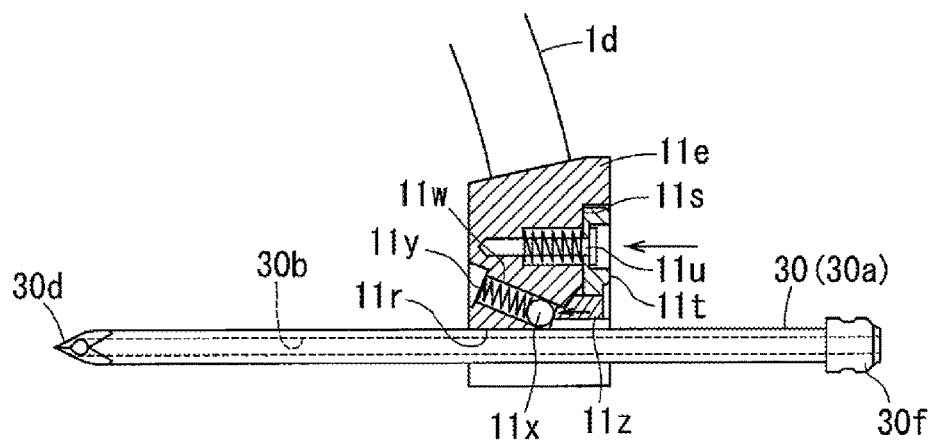

FIG. 22 is a side view of a guide pin piercing jig according to the other embodiment of the invention, FIG. 23 is a rear view of the guide pin piercing jig, FIGS. 24A and 24B are a plan view and a side view, respectively, of plural guide pin insertion cylinders of a rear cylinder unit (another example), and FIGS. 25A-25B are sectional views of a rear end portion of a frame of the guide pin piercing jig that is holding the plural guide pin insertion cylinders of a rear cylinder unit of the rear cylinder unit in a slidable manner. FIG. 25A shows a state that the guide pin insertion cylinders are locked so as not to be slidable rearward, and FIG. 25B shows a state the guide pin insertion cylinders are unlocked so as to be slidable rearward.

The guide pin piercing jig 11 according to this embodiment is different from the guide pin piercing jig 10 according to the above embodiment in the configurations of a rear cylinder unit 30 and a rear-end attachment portion 11e of a frame 1.

More specifically, as shown in FIGS. 24A and 24B, in the rear cylinder unit 30 of this embodiment, plural (two) parallel guide pin insertion cylinders 30a having straight cylinder holes 30b through which to insert guide pins, respectively, are provided integrally with each other. The rear cylinder unit 30 is a flat cylinder unit which has an elliptical sectional shape and contains the two parallel cylinder holes 30b through which to insert guide pins. A tip portion of the rear cylinder unit 30 is shaped into an end portion 30d which is sharp like an arrowhead and serves as a tentative fixing unit. A rear end portion of the rear cylinder unit 30 is a stopper portion 30f which is one-size thicker.

On the other hand, as shown in FIGS. 22, 23, and 25A-25B, the rear-end attachment portion 11e of the frame 1 is formed with a button housing recess 11s which houses a push button 11t. The push button 11t is provided with a pusher 11z for pushing a sphere 11x (described later) at the bottom. A screw 11u is screwed into a screw hole through a center hole of the push button 11t and the inside space of a compression coil spring 11v disposed behind the push button 11t. The push button 11t is urged by the compression coil spring 11v in such a direction as to be pushed out. Therefore, a certain gap is secured between the push button 11t and the bottom face of the button housing recess 11s and the push button 11t can be pushed in against the resilient force of the compression coil spring 11v until hitting the bottom face of the button housing recess 11s.

An insertion hole 11r having an elliptical sectional shape (and being continuous with a slit at the bottom) into which to insert the rear cylinder unit 30 is formed through a bottom portion of the attachment portion 11e so as to extend toward the center of the imaginary circle of the frame 1. A communication hole 11w which communicates with the insertion hole 11r from obliquely above houses the sphere 11x and a compression coil spring 11y. Because of the resilient force of the compression coil spring 11y, the sphere 11x is in contact with the tip of the pusher 11z and projects slightly into the insertion hole 11r. When the push button 11t is pushed by a fingertip, the pusher 11z is moved together with the push button 11t and pushes the sphere 11x to the deep side in the communication hole 11w.

Therefore, as shown in FIG. 25A, when the rear cylinder unit 30 is inserted into the insertion hole 11r of the attachment portion 11e from behind, the sphere 11x is pushed up by the rear cylinder unit 30 and goes inward in the communication hole 11w. As a result, the rear cylinder unit 30 can be inserted into the attachment portion 11e until the stopper portion 30f of the rear cylinder unit 30 hits the wall surface of the attachment portion 11e. On the other hand, an attempt to pull out the rear cylinder unit 30 fails because the sphere 11x bites into the tip of the pusher 11z and the top surface of the rear cylinder unit 30 as if to go into a gap formed between them.

In contrast, as shown in FIG. 25B, when the push button 11t is pushed with a fingertip, the pusher 11z is moved together with the push button 11t and the tip of the pusher 11z pushes the sphere 11x to the deep side in the communication hole 11w against the resilient force of the compression coil spring 11y and hence the rear cylinder unit 30 can be pulled out easily.

The other part of the configuration of the guide pin piercing jig 11 according to this embodiment is the same as the corresponding part of the guide pin piercing jig 10 according to the above embodiment, and hence will not be described redundantly by assigning the same symbols to the same members shown in FIGS. 22 to 25B.

In ACL reconstruction, like the guide pin piercing jig 10 according to the above embodiment, the guide pin piercing jig 11 according to this embodiment enables the following work. The front cylinder unit 2 is inserted into the knee joint from the front side. The tip boring aiming portion 2b of the front cylinder unit 2 is positioned by applying it to a proper portion (i.e., a portion, having a curved slant surface 20a, of a thighbone bottom surface), to which to bore a bone tunnel, of a thighbone bottom portion 20. The rear cylinder unit 30 is fixed tentatively by inserting it into the insertion hole 11r of the rear-end attachment portion 11e of the frame 1 and sticking the sharp end portion 30d of the rear cylinder unit 30 into the thighbone bottom portion 20 from obliquely behind. The thighbone bottom portion 20 is pierced with two guide pins 6 inserted through the two respective guide pin insertion holes 30b until they reach the boring aiming portion 2b. In this manner, the two guide pins 6 for hollow drills can pierce the thighbone bottom portion 20 through which to bore a bone tunnel, from obliquely behind to its proper portion in a proper direction. Subsequently, two bone tunnels 7 are bored through the thighbone bottom portion 20 by the hollow drills from behind along the respective guide pins 6. The two bone tunnels 7 are connected to each other by boring a tunnel 7a between them, and a connected bone tunnel is cut into a rectangular or elliptical shape. As a result, a rectangular or elliptical bone tunnel that is suitable for tendon transplantation can be formed.

Although the invention has been described in detail by referring to the particular embodiments, it is apparent to those skilled in the art that various changes and modifications are possible without departing from the spirit and scope of the invention.

The present application is based on Japanese Patent Application No. 2013-241760 filed on Nov. 22, 2013, the content of which is incorporated herein by reference.

The invention claimed is:

1. A guide pin piercing jig for piercing a living body bone with guide pins for boring holes in such a manner as to determine positions and a direction of the guide pins, the guide pin piercing jig comprising:
   a curved frame with a frame curved central axis;
   a front cylinder unit provided at a front end of the frame; and
   a rear cylinder unit provided at a rear end of the frame,
   wherein the front cylinder unit has a cylindrical portion, a base portion located at a first end of the cylindrical portion, and a boring aiming portion located at a second end of the cylindrical portion opposite to the first end, a cylinder hole passes through the base portion and the cylindrical portion, the boring aiming portion has an opening, the cylinder hole and the opening have a common central axis, and the boring aiming portion includes a positioning projection that extends in a direction that is parallel to the common central axis,
   the rear cylinder unit has a plurality of parallel guide pin insertion cylinders into which to insert the guide pins and a tentative fixing unit provided at a tip of the guide pin insertion cylinders, and
   the rear cylinder unit is slidable, with respect to the frame, in a straight line extending from an end of the frame curved central axis so as to be directed to the boring aiming portion.

2. The guide pin piercing jig according to claim 1, wherein respective center axes of the plurality of parallel guide pin insertion cylinders of the rear cylinder unit pass through the opening of the boring aiming portion.

3. The guide pin piercing jig according to claim 1, wherein a tip surface of the boring aiming portion is inclined from the common center axis.

4. The guide pin piercing jig according to claim 1, wherein the front cylinder unit is attached to the front end of the frame in a detachable manner.

5. The guide pin piercing jig according to claim 1, wherein the rear cylinder unit is attached to the rear end of the frame in a detachable manner.

6. The guide pin piercing jig according to claim 1, wherein each of the plurality of guide pin insertion cylinders of the rear cylinder unit has a straight cylinder hole.

7. The guide pin piercing jig according to claim 1, wherein the common center axis and each of center axes of the plurality of guide pin insertion cylinders of the rear cylinder unit cross each other at an angle of larger than 90° and smaller than 180°.

8. The guide pin piercing jig according to claim 1, wherein the cylinder hole extends along a central axis of the front cylinder unit.

9. The guide pin piercing jig according to claim 1, wherein the opening of the boring aiming portion is coaxial with a central axis of the front cylinder unit.

10. The guide pin piercing jig according to claim 1, wherein the positioning projection is a pair of positioning projections separated from each other and located at opposite sides of the boring aiming portion.

11. The guide pin piercing jig according to claim 1, wherein the parallel guide pin insertion cylinders extend through a tip of the rear cylinder unit.

12. The guide pin piercing jig according to claim 1, wherein the parallel guide pin insertion cylinders extend through a tip of the rear cylinder unit, and the tentative fixing unit is a sharp end of the tip and surrounds the parallel guide pin insertion cylinders.

13. The guide pin piercing jig according to claim 1, wherein a shape of the cylinder hole that passes through the base portion and the cylindrical portion is different than a shape of opening of the boring aiming portion in cross-section along a plane that is perpendicular to the common central axis.

* * * * *